(12) United States Patent
Mai

(10) Patent No.: US 9,526,768 B2
(45) Date of Patent: Dec. 27, 2016

(54) COMPOSITIONS FOR THE TREATMENT OF CANCER

(71) Applicant: Jennifer Mai, Seattle, WA (US)

(72) Inventor: Jennifer Mai, Seattle, WA (US)

(*) Notice: Subject to any disclaimer, the term of this patent is extended or adjusted under 35 U.S.C. 154(b) by 0 days.

(21) Appl. No.: 14/541,019

(22) Filed: Nov. 13, 2014

(65) Prior Publication Data

US 2016/0136249 A1    May 19, 2016

(51) Int. Cl.
| | | |
|---|---|---|
| *A61K 38/48* | (2006.01) | |
| *A61K 9/00* | (2006.01) | |
| *C12N 9/50* | (2006.01) | |

(52) U.S. Cl.
CPC ......... *A61K 38/4873* (2013.01); *A61K 9/0095* (2013.01); *C12N 9/63* (2013.01); *C12Y 304/22014* (2013.01); *C12Y 304/22033* (2013.01); *C12Y 304/22067* (2013.01)

(58) Field of Classification Search
CPC .......................................... C12N 9/63
USPC .......................................... 435/23
See application file for complete search history.

(56) References Cited

U.S. PATENT DOCUMENTS

| | | | | |
|---|---|---|---|---|
| 2007/0065556 | A1* | 3/2007 | Martin, Jr. ............... | A23G 9/38 426/565 |
| 2007/0259059 | A1* | 11/2007 | Eidenberger ......... | A61K 9/4875 424/769 |
| 2013/0236445 | A1* | 9/2013 | Liao ................... | A61K 38/4873 424/94.65 |

FOREIGN PATENT DOCUMENTS

| | | |
|---|---|---|
| CN | 102660427 B | 5/2013 |
| CN | 103504108 A | 1/2014 |
| WO | 96/33208 A1 | 10/1996 |
| WO | 00/26230 A1 | 5/2000 |
| WO | 00/44241 A1 | 8/2000 |
| WO | 01/34646 A2 | 5/2001 |
| WO | 01/34647 A2 | 5/2001 |
| WO | 01/34801 A2 | 5/2001 |
| WO | 01/65936 A1 | 9/2001 |
| WO | 02/102831 A1 | 12/2002 |
| WO | 03/060103 A2 | 7/2003 |
| WO | 03/074649 A1 | 9/2003 |
| WO | 2004/069211 A2 | 8/2004 |
| WO | 2007/144554 A2 | 12/2007 |
| WO | 2010/102284 A2 | 9/2010 |
| WO | 2010/128117 A1 | 11/2010 |
| WO | 2011/017093 A1 | 2/2011 |
| WO | 2012/068209 A2 | 5/2012 |
| WO | 2012/176172 A2 | 12/2012 |

OTHER PUBLICATIONS

Hayashi et al. "Protease immobilization onto porous chitosan beads", J of Applied Polymer Science, 1991, 42:85-92.*
Jacobsen "Soup or salad: investigating the action of enzymes in fruit on gelatin", J Chem Ed. 1999, 76(5):624A-624B.*
Grunden et al. "Effects of proteolytic enzymes on the functionality of chicken egg albumen", J of Food Science, 1974, 39:841-843.*
Route of administration, Mosby's Medical Dictionary, 2009, p. 1.*
Heinicke et al. Economic Botany, 1957, 11(3):225-234.*
Taussig et al. J of Ethnopharmacology, 1988, 22:191-203.*
Karna et al. Br J Nutr., 2012, 107(5)473-484.*
Gortner et al. "The Coenzyme Requirement and Enzyme Inhibitors of Pineapple Indoleacelic Acid Oxidase," J. Biol. Chem. 1958, 233:731-735.
Kunze, R. et al., "Proteolytic Enzymes and Immune Modulation for Cancer Prevention and Treatment," International Cancer Chemo Prevention Conference, Apr. 28, 1993, pp. 58, 85.
Chobotova, K. et al., "Broinelain's Activity and Potential as an Anti-Cancer Agent: Current Evidence and Perspectives," Cancer Letters, Apr. 28, 2010, pp. 148-156, vol. 290, No. 2, New York, US.
PCT, "International Search Report and Written Opinion" issued in corresponding International Application No. PCT/US2015/058139, mail date Jan. 21, 2016.

* cited by examiner

*Primary Examiner* — Bin Shen
(74) *Attorney, Agent, or Firm* — Procopio, Cory, Hargreaves & Savitch LLP

(57) ABSTRACT

The present invention relates to novel compositions comprising proteolytic enzymes and fining agents as well as methods for the treatment and/or prevention of cancer using these compositions.

4 Claims, 10 Drawing Sheets

US 9,526,768 B2

COMPOSITIONS FOR THE TREATMENT OF CANCER

FIELD OF THE INVENTION

The present invention relates to novel compositions comprising proteolytic enzymes and fining agents as well as methods for the treatment and/or prevention of cancer using these compositions.

BACKGROUND OF THE INVENTION

Select natural and synthetic digestive (proteolytic) enzymes are used to artificially interact with resilient extracellular matrix models to observe if proteins in the extracellular matrix can be broken down. Therefore, if the extracellular matrix can be broken down, organic compounds (fining agents) can be used to make ionic bonds with the products from the matrix degradation to perform a lysing process to remove them.

Provided herein are novel compositions comprising at least one proteolytic enzyme and a fining agent. Also provided are methods for treating cancer with these novel compositions.

SUMMARY OF THE INVENTION

In some of the embodiments disclosed herein, the mammal is a human. In some embodiments disclosed herein, the mammal is a dog, cat, horse or bird.

In some embodiments, the compositions provided herein are orally administered. In other embodiments, the compositions provided herein are administered intravenously.

Also provided herein are articles of manufacture, which include packaging material, the enzymes and fining agents described herein within the packaging material, and a label that indicates that the composition is used for the treatment, prevention or amelioration of one or more symptoms of a disease or condition being treated.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The details of the present invention may be gleaned in part by study of the accompanying figures all of which are photographs taken after 24 hours of treatment and at 200×, in which.

DETAILED DESCRIPTION OF THE INVENTION

Figure 1:
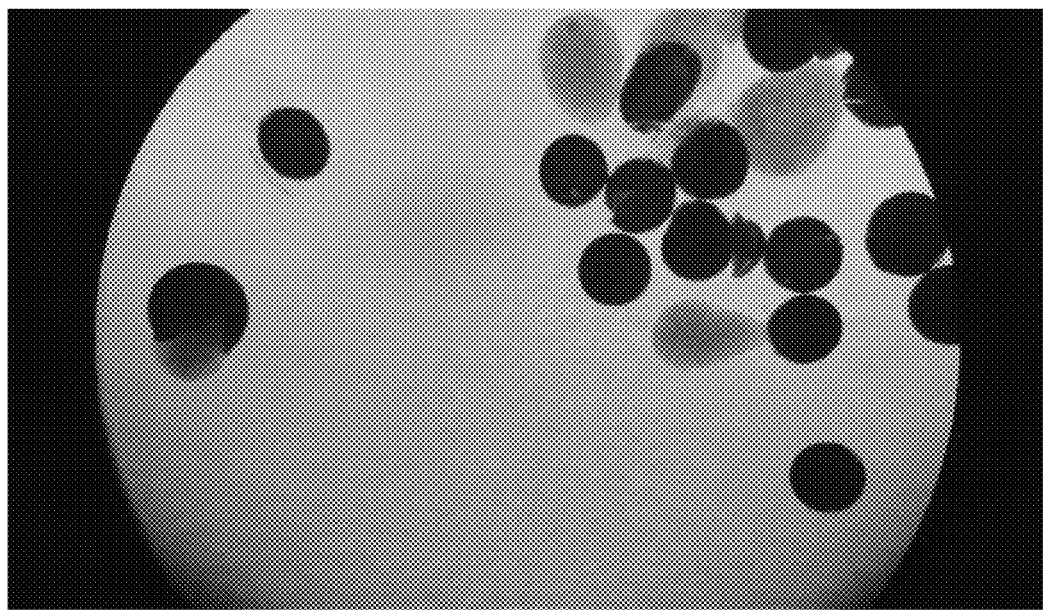
FIG. 1: Control photo—In the control, the cysts are grown for 24 hours only in deionized water with no other treatments. Presence of hatching is evident by a singular crack down the middle of the shell to create a partial parting line and opening for hatching. There is also presence of intact, hatching nauplii, which indicates that the nauplii are able to survive in this artificial environment (normal conditions need saline/saltwater conditions). The shells show no signs of deterioration patterns of any kind and remain solid in color throughout. The cysts remain dark brown colored in their shells. This demonstrates that the cysts can be grown in deionized water without any factors affecting its growth as well as deionized water does not contribute to deterioration of the cyst shells, or extracellular matrix.
Figure 2:
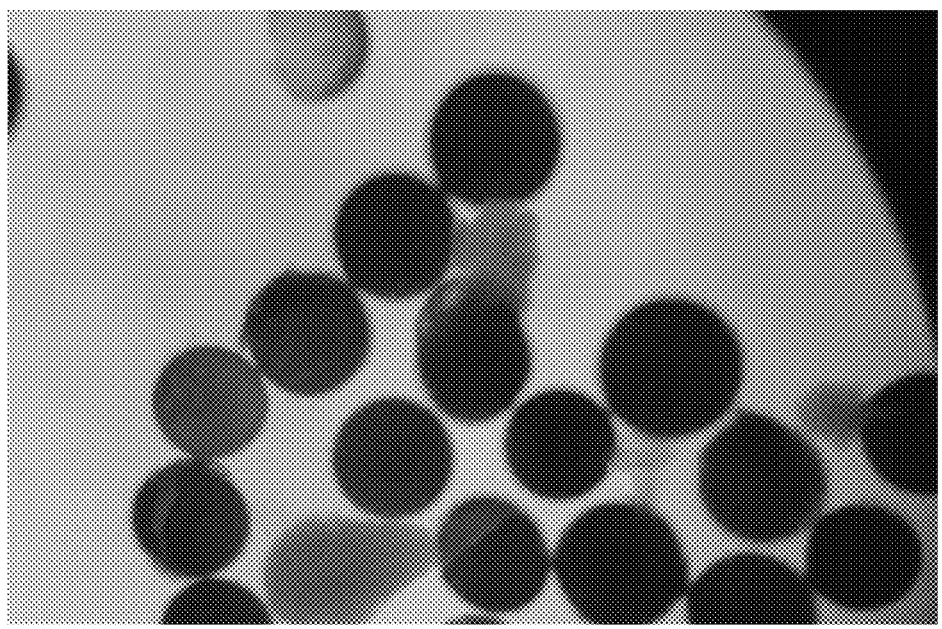
FIG. 2: Kiwi. After treating the cysts with the kiwi juice for 24 hours, the inside of cyst shells can be seen to show development of nauplii, as seen by the circular dot in the center of the cyst on some of the cysts. There is one, hatching, intact nauplii (pear shaped) and one destroyed nauplii (squiggly mass) for comparison. Presence of lighter shells can be seen, which shows different cyst shell color gradients other than original pre-treatment dark brown as seen in the control (FIG. 1). Different netting or sponge-like deterioration patterns can be seen where the netting portions are darker in color on top of lighter overall whole cyst shells. There is also a clear section of a cyst shell that can also be seen floating about in the medium, which indicates that there is deterioration occurring to the main cyst shells causing a thin later to separate. This is different from regular hatching that results in whole dark brown shell halves.
Figure 3:
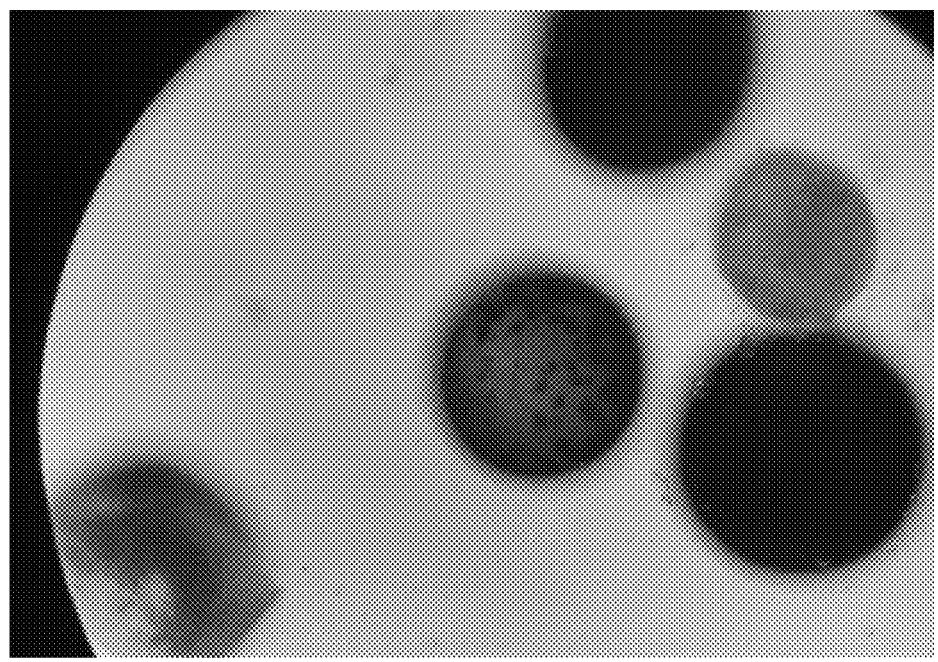
FIG. 3: Kiwiberry. After treating these cysts for 24 hours, a few differences can be observed. Clear-like, with some portions of rounded edges, cyst shell pieces can be seen floating about the medium. This indicates that portions of the cyst's shell are being detached, which is different from hatching shelf halves that are dark brown in color (FIG. 1). A deterioration pattern can be seen on the one cyst in the photo with the semi-transparent body with the dark brown spots littered about it. The cyst is intact as whole while the deterioration is ongoing on the shell. This indicates that there is no effect done on the structural integrity of the main cyst. Other cysts that can be seen in the photo are still relatively solid dark brown with no deterioration patterns present yet.
Figure 4:
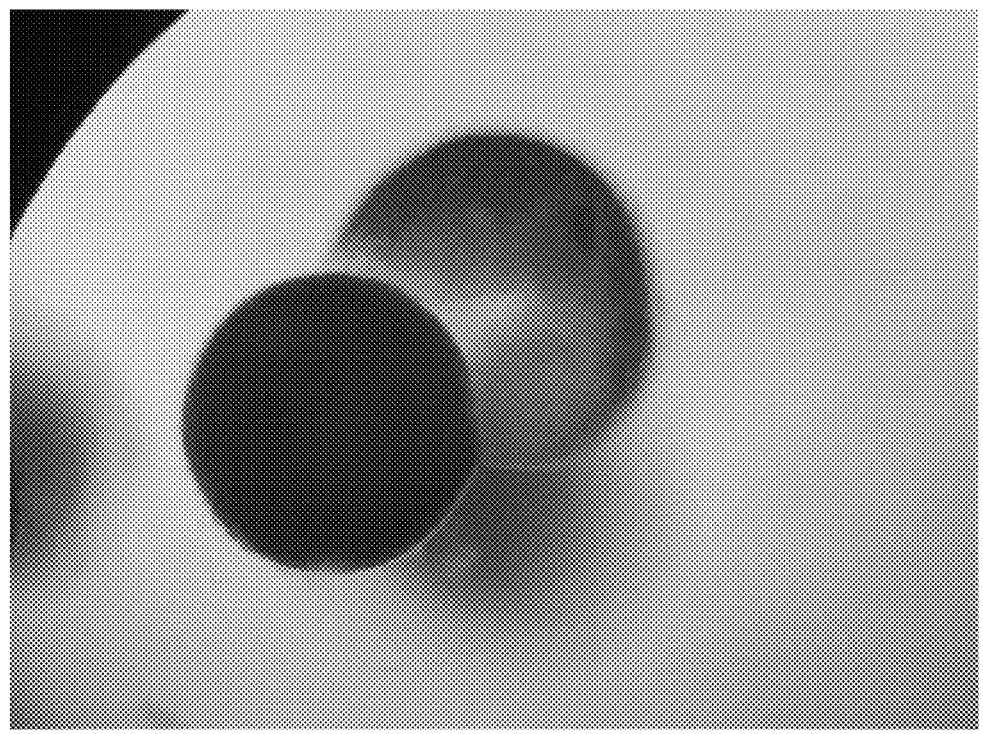
FIG. 4: Kiwiberry. A continuation of FIG. 3, from the same results, different section. A clear cyst shell layer is being detached from the main cyst that appears to be a lighter shade of brown compared to FIG. 1. This clear-like shell fragment with rounded edges indicates that it had previously encompassed the cyst it was on. The clear-like shell is vastly different than the regular nauplii hatched shell that results in only dark brown shell halves. The cyst that is left behind from the clear fragment is also smaller in shape.
Figure 5:
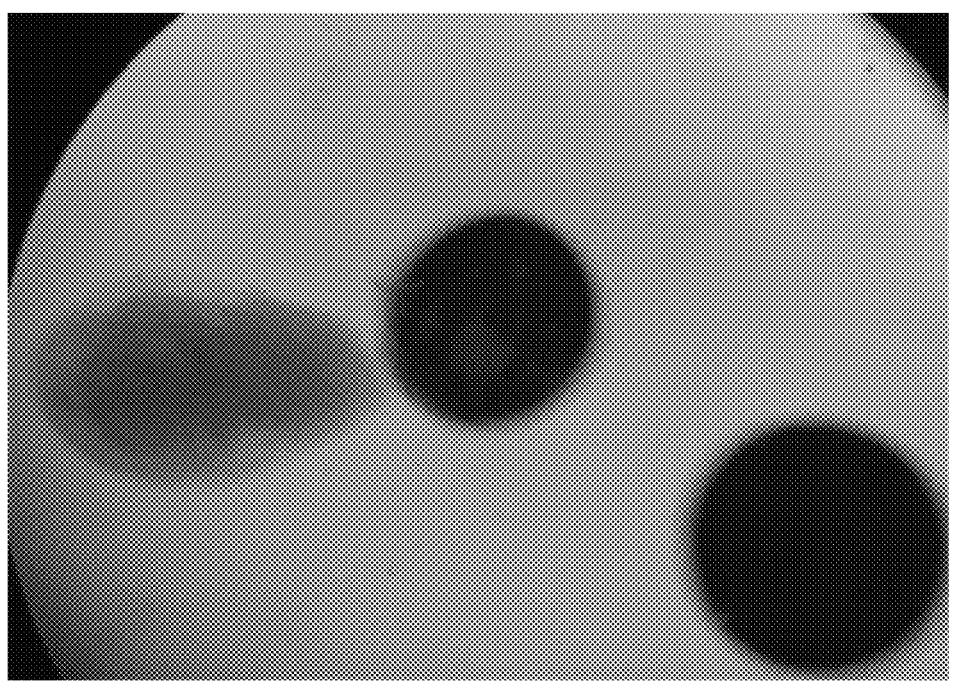
FIG. 5: Kiwiberry. A continuation of FIG. 3, from the same results, different section. An intact nauplii can be seen hatching from a cyst, indicating that it can survive in current treatment conditions. On the same cyst that is producing the hatching nauplii, deterioration patterns can be seen on the shell, while hatching of the nauplii is occurring, unaffecting the hatching process. The deterioration pattern here consists of different sized patches missing from the rounded cyst's dark brown shell, revealing a lighter colored internal body. There is another cyst in the same photo as seen in the lower right that is unaffected by the treatment yet, still remaining solid dark brown with no deterioration patterns of any kind.
Figure 6:
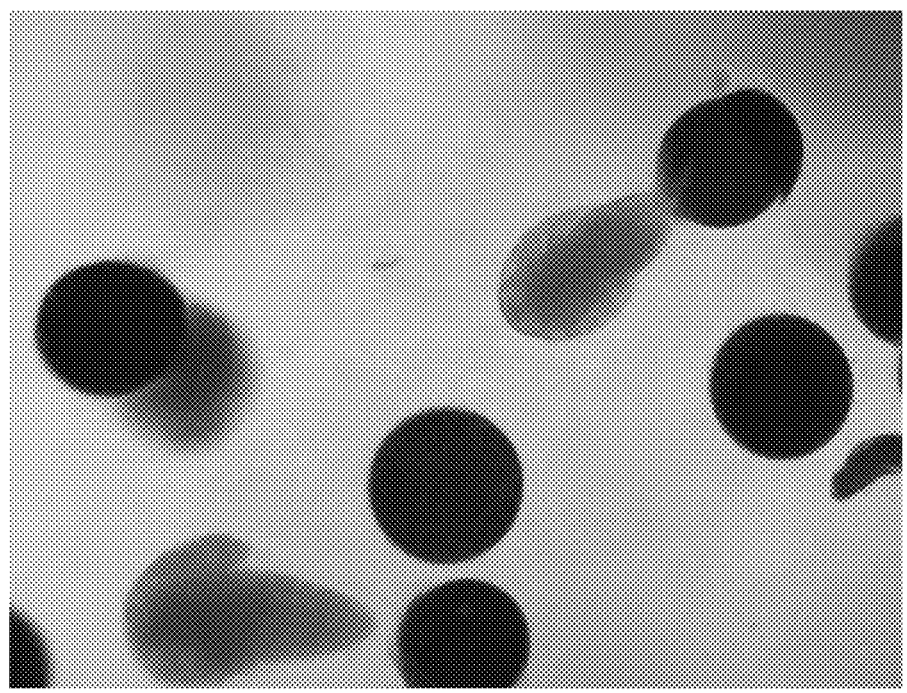
FIG. 6: Banana. After 24 hours of treatment, different notable observations can be made. Different cyst gradients are seen from dark brown to medium or a lighter brown. Intact, hatching nauplii are seen, which indicates that it is able to survive and thrive in current treatment conditions. The cyst in the top right corner of the photo demonstrates a cyst that exhibits a "cap" like detachment and deterioration, where whole pieces of shell are detached from the main cell. The main cell, lighter in color than the "cap" piece detaching, is able to hatch with a different parting line, unaffected by the deterioration process. There is also a cyst with a netting or sponge-like deterioration pattern with a dark netting pattern on top of a lighter brown body.
Figure 7:
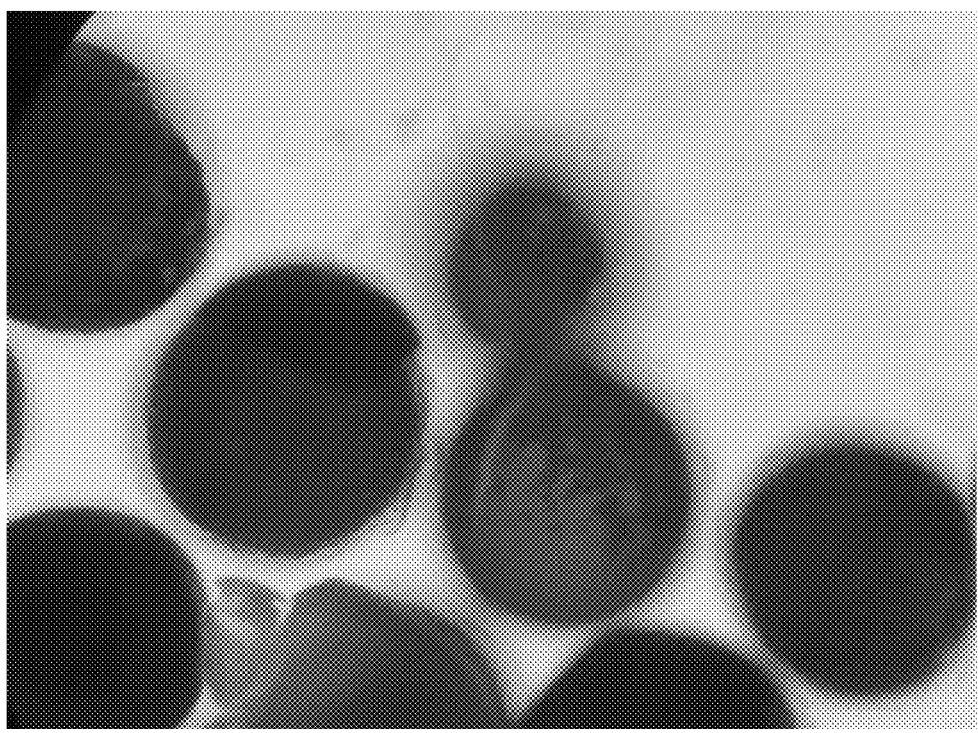
FIG. 7. Kieselsol. After 24 hours of treatment, different deterioration patterns are seen. On one of the cysts, a "cap" like larger fragments is seen being lifted from the cyst. The fragment that is being lifted off of the cyst is dark brown in color while the rest of the whole, intact cyst is lighter brown in color. The shape of the fragment detaching from the cyst is also different in shape compared to normal hatching cyst shell halves as seen in FIG. 1. Another cyst is seen with a gradient, sponge-like deterioration pattern, where the sponge-like pattern is dark brown on top of the lighter, translucent brown, whole, intact, cyst. That cyst is currently actively hatching with a clear parting line that can be seen with a nauplii hatching in the distance. There are other cyst sells in the photo with different color ranges from dark brown to a medium brown.
Figure 8:
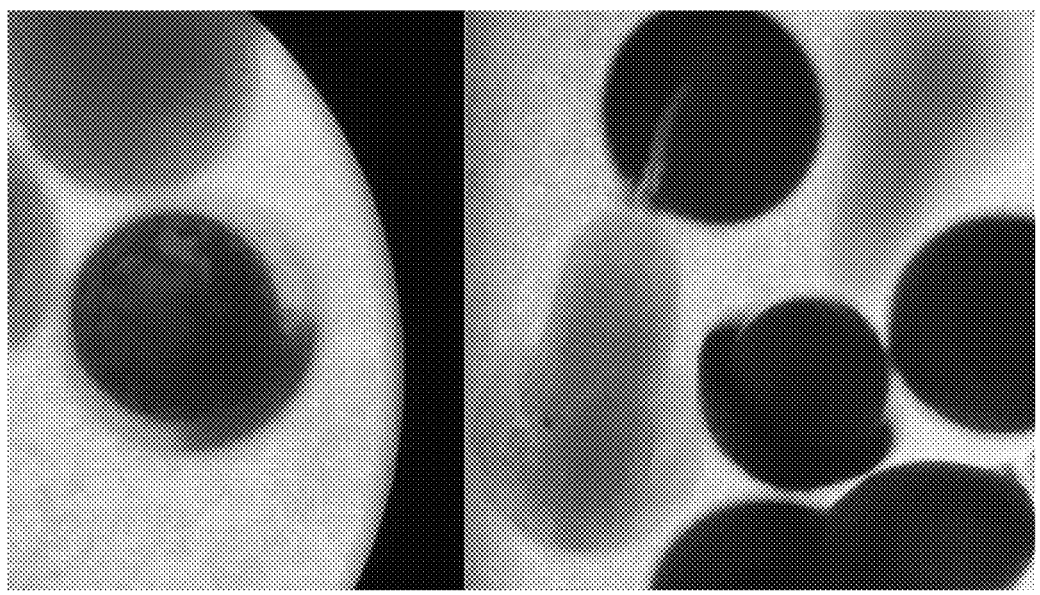
FIG. 8. Kieselsol. A continuation of FIG. 7, from the same results, different section. Most cysts seen in this photo are of a lighter brown compared to those of FIG. 1. Intact, hatching nauplii indicates that the cysts can thrive and survive in the current treatment conditions. An entire clear shell encompassing a cyst is seen while active deterioration is occurring with missing dark patches revealing a lighter brown, translucent cyst underneath. Another cyst with a "cap" like deteriorated portion is seen while the cyst is hatching in the right half of the photo. The cyst that remains has a glossy like texture that picks up a bit of light reflection unlike the other cysts around it.
Figure 9:
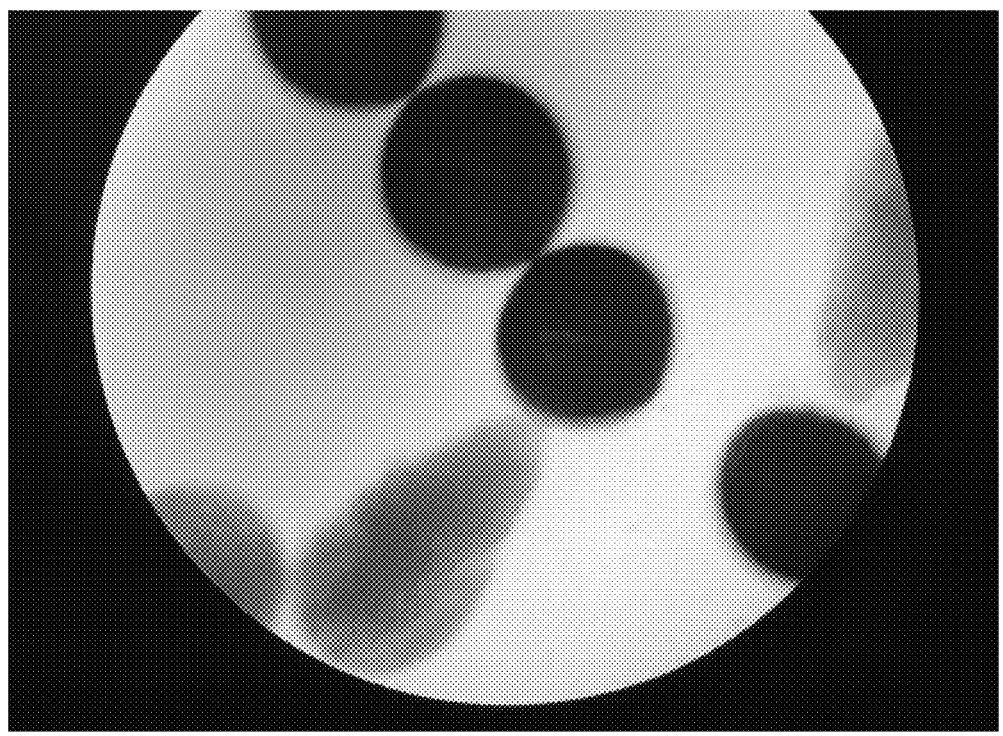
FIG. 9. Pineapple+Ginger+Albumen. Using the combined enzymes and fining agent after 24 hours, the nauplii are able to hatch, stay intact and survive in the current treatment condition. No damaged nauplii are seen. The seemingly dark cyst shells also have faint light cracking patterns seen against the medium dark brown shell color, demonstrating a deterioration going on while active hatching is occurring. The deterioration process does not affect the hatching or growth processes.
Figure 10:
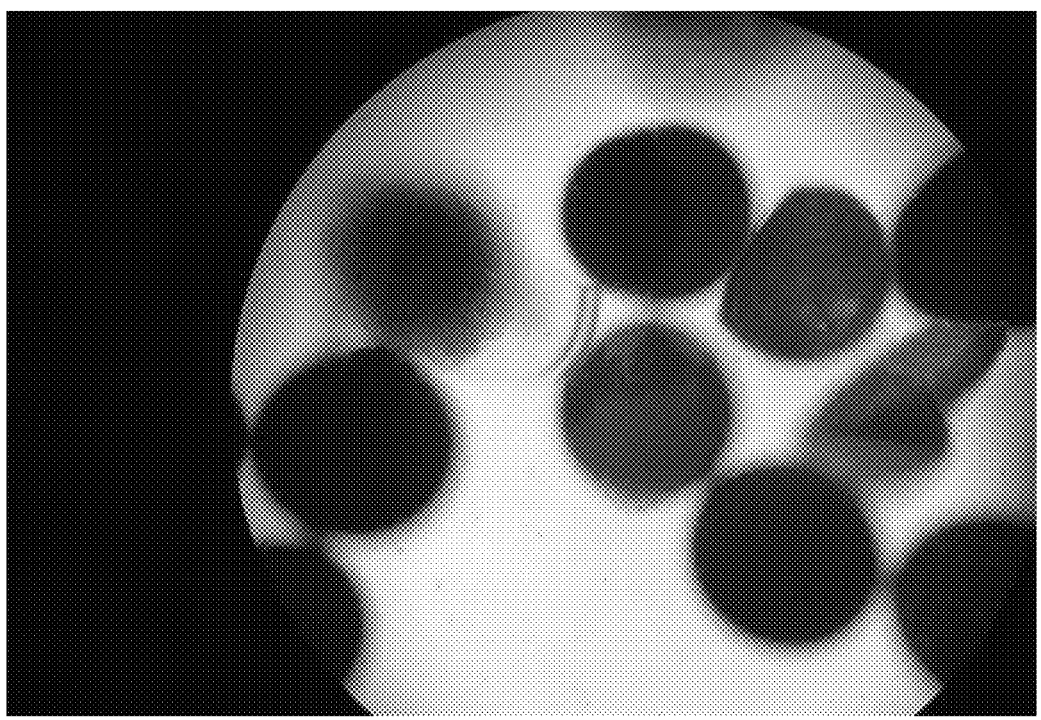
FIG. 10. Pineapple+Ginger+Albumen. A continuation of FIG. 9, same result from treatment, different section. Whole cyst cell shapes are seen intact; however, the dark brown shell coat is deteriorating, revealing a lighter brown, semi-translucent whole cyst underneath. This is occurring to a few different cysts as seen in the photo. There are also a few remnants of the detached and deteriorated dark brown coats floating about, which is different from a hatched shell half as seen in FIG. 1. There are netting or sponge-like deterioration patterns seen as well as detaching lifting off of the cyst pieces compared to the few still solid dark brown cysts.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description presented herein represents a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

Select natural and synthetic digestive (proteolytic) enzymes are used to artificially interact with resilient extracellular matrix models to observe if proteins in the extracellular matrix can be broken down. Therefore, if the extracellular matrix can be broken down, organic compounds (fining agents) can be used to make ionic bonds with the products from the matrix degradation to perform a lysing process to remove them.

Digestive enzymes are a naturally occurring feature in all species of life—functioning as a mechanism to selectively break down large or complex macromolecules into smaller, more useful molecules such as nutrients that can be extracted for digestive reasons that the body can recognize. A series of digestive enzymes from natural and synthetic sources were tested against the extracellular matrix of *Artemia salina*. *A. salina* can remain dormant in their cyst state, relatively unharmed. Their extracellular matrix protects the larvae, or nauplii, from hatching for upwards of over two decades. These various digestive enzymes were chosen to study the artificial effects it has on the extracellular matrix of *A. salina*, to see if the extracellular matrix can be safely dissolved to expose the nauplii undergoing mitosis intact.

A small cluster of *A. salina* dormant cysts were grown in vivo, each trial within Petri dishes at various conditions and treatments to serve as a ubiquitous model in studying malignant like tumor conditions before actual testing on humans. A control for each trial run was set up where a cluster of *A. salina* are grown without any treatment to its growth factor, only suspended in deionized water. A separate treatment of UV exposure tested against the control was used to illustrate the effects of the UV treatment affecting the extracellular matrix of the dormant cyst while in growth. Each digestive enzyme was solely tested on *A. salina* for its individual performance. Dilutions of each tested digestive enzyme were performed to find the optimal concentration for the enzymes' effect on the surface area of the extracellular matrix. Observations were made every day to record any notable changes. Choices of enzymes were chosen for their known digestive properties, but were either eliminated or diluted based on the state of the extracellular matrix of *A. salina*.

It was found that diluted, naturally sourced digestive enzymes disintegrate the extracellular matrix of *A. salina* quicker and in a lower concentration with less destruction to the growth of the nauplii. A clear membrane was left surrounding the nauplii. Under a microscopic light source, mitotic growth of the nauplii can be seen until they hatch. Main indicators of success were a dissolved extracellular matrix where the inside of the cyst could be seen to fully hatched, motile, grown *A. salina*. Synthetic sources of digestive enzymes also demonstrated dissolving of the extracellular matrix and viewing of the unhatched nauplii. Organic compounds that were tested for their function with the extracellular matrix of *A. salina* showed visible deterioration patterns unlike the digestive enzymes, which resulted in a smooth, gradual deterioration of the extracellular matrix.

Accordingly, it was discovered that taking digestive enzymes to artificially break down extracellular matrices can be done in combination usage with organic compounds to further break down parts of the extracellular matrix while keeping the rest of the cell intact and alive. There are sustainable and naturally founding digestive enzymes and organic compounds that can be used to dissolve these extracellular matrices in *A. salina*, therefore, these enzymes can be used as a viable model for dissolving malignant tumors safely in humans with further human testing.

CERTAIN EXEMPLARY TERMINOLOGY

Unless defined otherwise, all technical and scientific terms used herein have the same meaning as is commonly understood by one of skill in the art to which the claimed subject matter belongs. In the event that there is a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless otherwise stated. Furthermore, use of the term "including" as well as other forms, such as "include", "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

It is to be understood that the methods and compositions described herein are not limited to the particular methodology, protocols, and reagents described herein and as such may vary. It is also to be understood that the terminology used herein is for the purpose of describing particular embodiments only, and is not intended to limit the scope of the methods and compositions described herein. Numerous variations, changes, and substitutions will now occur to those skilled in the art without departing from the invention. It should be understood that various alternatives to the embodiments of the invention described herein may be employed in practicing the invention. It is intended that the appended claims define the scope of the invention and that methods and structures within the scope of these claims and their equivalents be covered thereby.

Unless defined otherwise, all technical and scientific terms used herein have the same meaning as is commonly understood by one of skill in the art to which this invention belongs.

The term "acceptable" with respect to a formulation, composition or ingredient, as used herein, means having no persistent detrimental effect on the general health of the subject being treated.

As used herein, amelioration of the symptoms of a particular disease, disorder or condition by administration of a particular pharmaceutical composition refers to any lessening of severity, delay in onset, slowing of progression, or shortening of duration, whether permanent or temporary, lasting or transient that can be attributed to or associated with administration of the compound or composition.

The terms "administer," "administering", "administration," and the like, as used herein, refer to the methods that may be used to enable delivery of compositions to the desired site of biological action. These methods include, but are not limited to oral routes, intraduodenal routes, parenteral injection (including intravenous, subcutaneous, intraperitoneal, intramuscular, intravascular, and/or infusion), topical and rectal administration. Those of skill in the art are familiar with administration techniques that can be employed with the compositions and methods described herein. In some embodiments, the compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time. Co-administration includes simultaneous administration in separate compositions, administration at different times in separate compositions, or administration in a composition in which both agents are present.

The terms "effective amount" or "therapeutically effective amount," as used herein, refer to a sufficient amount of an agent being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising the enzymes and fining agents as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients and a co-agent, are both administered to a patient simultaneously in the form of a single entity or dosage. The term "non-fixed combination" means that the active ingredients and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," as used herein, include alleviating, abating or ameliorating a disease or condition, symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. The treatment or amelioration of symptoms can be based on objective or subjective parameters; including the results of a physical examination, functional (self) evaluation, and/or any form of vision evaluation.

The term "in vivo" refers to an event that takes place in a subject's body.

Cancer

In some embodiments, disclosed herein are methods of treating cancer with a composition disclosed herein.

The term "cancer" as used herein, refers to an abnormal growth of cells that tend to proliferate in an uncontrolled way and, in some cases, to metastasize (spread). Types of cancer include, but are not limited to, solid tumors (such as those of the bladder, bowel, brain, breast, endometrium, heart, kidney, lung, liver, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, desmoid tumors, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, Hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Sezary syndrome, skin cancer, small cell lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and Wilms tumor.

In some embodiments, a composition disclosed herein, is used in the treatment of ovarian cancer, prostate cancer, breast cancer, lung cancer, melanoma, head and neck cancer, bowel cancer (colorectal cancer), thyroid cancer, glioblastoma, follicular lymphoma, renal cancer, Hodgkin lymphoma, hepatocellular carcinoma, pancreatic cancer or melanoma.

In some embodiments, a composition disclosed herein, is used in the treatment of bone metastases.

In some embodiments, a composition disclosed herein, is used in the treatment of oral cancer, prostate cancer, rectal cancer, non-small cell lung cancer, lip and oral cavity cancer, liver cancer, lung cancer, anal cancer, kidney cancer, vulvar cancer, breast cancer, oropharyngeal cancer, nasal cavity and paranasal sinus cancer, nasopharyngeal cancer, urethra cancer, small intestine cancer, bile duct cancer, bladder cancer, ovarian cancer, laryngeal cancer, hypopharyngeal cancer, gallbladder cancer, colon cancer, colorectal cancer, head and neck cancer, parathyroid cancer, penile cancer, vaginal cancer, thyroid cancer, pancreatic cancer, esophageal cancer, Hodgkin's lymphoma, leukemia-related disorders, mycosis fungoides, or myelodysplastic syndrome.

In some embodiments, a composition disclosed herein, is used in the treatment of non-small cell lung cancer, pancreatic cancer, breast cancer, ovarian cancer, colorectal cancer, or head and neck cancer.

In some embodiments, a composition disclosed herein, is used in the treatment of a carcinoma, a tumor, a neoplasm, a lymphoma, a melanoma, a glioma, a sarcoma, or a blastoma.

In some embodiments, the carcinoma is selected from the group consisting of: carcinoma, adenocarcinoma, adenoid cystic carcinoma, adenosquamous carcinoma, adrenocortical carcinoma, well differentiated carcinoma, squamous cell carcinoma, serous carcinoma, small cell carcinoma, invasive squamous cell carcinoma, large cell carcinoma, islet cell carcinoma, oat cell carcinoma, squamous carcinoma, undifferentiated carcinoma, verrucous carcinoma, renal cell carcinoma, papillary serous adenocarcinoma, merkel cell carcinoma, hepatocellular carcinoma, soft tissue carcinomas, bronchial gland carcinomas, capillary carcinoma, bartholin gland carcinoma, basal cell carcinoma, carcinosarcoma, papilloma/carcinoma, clear cell carcinoma, endometrioid adenocarcinoma, mesothelial, metastatic carcinoma, mucoepidermoid carcinoma, cholangiocarcinoma, actinic keratoses, cystadenoma, and hepatic adenomatosis.

In some embodiments, the tumor is selected from the group consisting of: astrocytic tumors, malignant mesothelial tumors, ovarian germ cell tumor, supratentorial primitive neuroectodermal tumors, Wilm's tumor, pituitary tumors, extragonadal germ cell tumor, gastrinoma, germ cell tumors, gestational trophoblastic tumor, brain tumors, pineal and supratentorial primitive neuroectodermal tumors, pituitary tumor, somatostatin-secreting tumor, endodermal sinus tumor, carcinoids, central cerebral astrocytoma, glucagonoma, hepatic adenoma, insulinoma, medulloepithelioma, plasmacytoma, vipoma, and pheochromocytoma.

In some embodiments, the neoplasm is selected from the group consisting of: intaepithelial neoplasia, multiple myeloma/plasma cell neoplasm, plasma cell neoplasm, interepithelial squamous cell neoplasia, endometrial hyperplasia, focal nodular hyperplasia, hemangioendothelioma, lymphangioleio myomatosis and malignant thymoma.

In some embodiments, the lymphoma is selected from the group consisting of: nervous system lymphoma, AIDS-related lymphoma, cutaneous T-cell lymphoma, non-Hodgkin's lymphoma, mantle cell lymphoma, follicular lymphoma and Waldenstrom's macroglobulinemia.

In some embodiments, the melanoma is selected from the group consisting of: acral lentiginous melanoma, superficial spreading melanoma, uveal melanoma, lentigo maligna melanomas, melanoma, intraocular melanoma, adenocarcinoma nodular melanoma, and hemangioma.

In some embodiments, the sarcoma is selected from the group consisting of: adenomas, adenosarcoma, chondosarcoma, endometrial stromal sarcoma, Ewing's sarcoma, Kaposi's sarcoma, leiomyosarcoma, rhabdomyosarcoma, sarcoma, uterine sarcoma, osteosarcoma, and pseudosarcoma.

In some embodiments, the glioma is selected from the group consisting of: glioma, brain stem glioma, and hypothalamic and visual pathway glioma.

In some embodiments, the blastoma is selected from the group consisting of: pulmonary blastoma, pleuropulmonary blastoma, retinoblastoma, neuroblastoma, medulloblastoma, glioblastoma, and hemangiblastomas.

Exemplary Enzymes

In various embodiments provided herein, compositions comprising one or more natural and/or synthetic digestive (proteolytic) enzymes are used to break down resilient extracellular matrices.

Non-limiting examples of proteolytic enzymes useful in the present invention include the family of cystein proteases, which can be found in papain and chymopapain from papaya fruit, ficain in figs, actinidain in kiwifruit & Chinese gooseberry/mango/banana. Specific examples of fresh proteolytic enzymes useful in the present invention are in kiwi, kiwiberry, turmeric, papaya, banana+peel, mango, turmeric+ginger, and figs. Also useful are enzymes that function like a protease enzyme such as diarylheptanoid metabolite (curcumin from fresh turmeric). In specific embodiments, one or more of the enzymes are selected from bromelain, actinidain, ginger protease (GP) or zingipain.

Exemplary Fining Agents

Once the proteolytic enzymes break down the extracellular matrix into byproducts, the fining agents function to remove those byproducts. Another feature about fining agents is that they remove the byproducts ability to precipitate and or to bind proteins. Accordingly, in various embodiments provided herein, once the extracellular matrices are broke down, organic compounds such as fining agents are used to make ionic bonds with the products from the matrix degradation to perform a lysing process to remove them.

Non-limiting examples of fining agents useful in the compositions described herein are carbon, gelatin, casein, albumen, PVPP, isinglass (ichtyocolle), kieselsol, chitosan, kieselsol+chitosan, sodium alginate, diatomaceous earth, alginic acid, and bentonite. In specific embodiments the fining agent is albumen.

Exemplary Pharmaceutical Compositions

Pharmaceutical compositions may be formulated in a conventional manner using one or more physiologically acceptable carriers including excipients and auxiliaries which facilitate processing of the active components into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference in their entirety for such disclosure.

In some embodiments, the combination of enzymes and finning agents described herein are administered either alone or in combination with pharmaceutically acceptable carriers, excipients or diluents, in a pharmaceutical composition. Administration of the compositions described herein can be effected by any method that enables delivery of the enzymes and fining agents to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compositions described herein can be administered locally to the area in need of treatment, by for example, local infusion during surgery, topical application such as creams or ointments, injection, catheter, or implant. The administration can also be by direct injection at the site of a diseased tissue or organ.

Provided herein are pharmaceutical compositions that include the enzymes and fining agents described herein and a pharmaceutically acceptable diluent(s), excipient(s), and/or carrier(s). In addition, the compositions described herein can be mixed with other active ingredients, as in combination therapy.

A pharmaceutical composition, as used herein, refers to a mixture of one or more enzymes and fining agents described herein with other chemical components, such as carriers, stabilizers, diluents, dispersing agents, suspending agents, thickening agents, and/or excipients. The pharmaceutical composition facilitates administration of these components to an organism. In practicing the methods of treatment or use provided herein, therapeutically effective amounts of the enzymes and fining agents described herein are administered in a pharmaceutical composition to a mammal having a disease or condition to be treated. A therapeutically effective amount can vary widely depending on the severity of the disease, the age and relative health of the subject, the potency of the enzymes and fining agents used and other factors. The components in the compositions provided herein can be used singly or in combination with one or more therapeutic agents as components of mixtures.

Pharmaceutical compositions which can be used orally include tablets, sublingual tablets, chewable/dissolvable tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the enzymes and fining agents may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the compositions which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the enzymes and fining agents to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the enzymes and fining agents may be formulated with suitable polymeric or hydrophobic materials (for example, an emulsion in an acceptable oil) or ion exchange resins, or as sparingly soluble derivatives, for example, as a sparingly soluble salt.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the enzymes and fining agents and a suitable powder base such as lactose or starch. The powder composition may be presented in unit dosage form, in for example, capsules, cartridges, gelatin or blister packs from which the powder may be administered with the aid of an inhalator or insufflator.

The compositions described herein can be administered topically and can be formulated into a variety of topically administrable compositions, such as solutions, suspensions, lotions, gels, pastes, medicated sticks, balms, creams or ointments. Such pharmaceutical compositions can contain solubilizers, stabilizers, tonicity enhancing agents, buffers and preservatives known in the art.

Formulations suitable for transdermal administration of the compositions described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of the compositions described herein. The rate of absorption can be slowed by using rate-controlling membranes or by trapping the enzymes and fining agents within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

It should be understood that in addition to the ingredients particularly mentioned above, the compounds and compositions described herein may include other agents conventional in the art having regard to the type of formulation in question, for example those suitable for oral administration may include flavoring agents.

Pharmaceutical compositions may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. Pharmaceutical compositions that include a compound described herein may be manufactured in a conventional manner, such as, by way of example only, by means of conventional mixing, dissolving, granulating, dragee-making, levigating, emulsifying, encapsulating, entrapping or compression processes.

Aqueous suspensions can also contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Useful compositions can also include a mucoadhesive polymer, selected from, for example, carboxymethylcellulose, carbomer (acrylic acid polymer), poly(methylmethacrylate), polyacrylamide, polycarbophil, acrylic acid/butyl acrylate copolymer, sodium alginate, and dextran. Oral suspensions/liquids can be in a powder form until the user adds water. In various embodiments, the pharmaceutical composition is an oral Syrup or oral g/mL solution.

Compositions may also include solubilizing agents to aid in the solubility of an enzyme and/or fining agent described herein. The term "solubilizing agent" generally includes agents that result in formation of a micellar solution or a true solution of the agent. Certain acceptable nonionic surfactants, for example polysorbate 80, can be useful as solubilizing agents, as can ophthalmically acceptable glycols, polyglycols, e.g., polyethylene glycol 400, and glycol ethers.

Compositions may also include one or more pH adjusting agents or buffering agents, including acids such as acetic acid, boric acid, citric acid, lactic acid, phosphoric acid and hydrochloric acid; bases such as sodium hydroxide, sodium carbonate, sodium bicarbonate, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Other compositions may also include one or more preservatives to inhibit microbial activity. Suitable preservatives are known in the art and include, but are not limited to, mercury-containing substances such as merfen and thiomersal; stabilized chlorine dioxide; and quaternary ammonium compounds such as benzalkonium chloride, cetyltrimethylammonium bromide and cetylpyridinium chloride.

Still other compositions may include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other compositions may include one or more antioxidants to enhance chemical stability where required. Suitable antioxidants include, by way of example only, ascorbic acid and sodium metabisulfite.

In some embodiments, the compositions provided herein comprise a preservative. Non-limiting examples of preservatives useful in the present invention are parabens (alkyl esters of p-hydroxybenzoic acid, such as methyl- and propylparaben), zoic acid, sorbic acid, benzyl alcohol, phenoxyethanol, chlorocresol, benzalkonium chloride, centrimide, benzethonium chloride, chlorohexidine, chlorobutanol, methylparaben, phenylethyl alcohol, phenylmercuric acetate, phenylmercuric borate, phenylmercuric nitrate, propylparaben and thimersal.

An effective amount of a composition may vary based on a variety of factors, including but not limited to, the physiological characteristics of the subject, the nature of the condition to be treated, and the route and/or method of administration. Advantageously, methods described herein allow treatment of indications with reductions in side effects, dosage levels, dosage frequency, treatment duration, tolerability, and/or other factors.

Exemplary Methods of Dosing and Treatment Regimens

The compositions described herein can be used in the preparation of medicaments for the treatment or prevention of a specific disease or condition. In addition, a method for treating any of the diseases or conditions described herein in a subject in need of such treatment, involves administration of pharmaceutical compositions containing at least one enzymes and fining agent, in therapeutically effective amounts to said subject The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial).

In prophylactic applications, compositions containing the compounds described herein are administered to a patient susceptible to or otherwise at risk of a particular disease, disorder, or condition. Such an amount is defined to be a "prophylactically effective amount or dose." In this use, the precise amounts also depend on the patient's state of health, weight, and the like. It is considered well within the skill of the art for one to determine such prophylactically effective amounts by routine experimentation (e.g., a dose escalation clinical trial). When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds described herein may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds described herein may be given continuously; alternatively, the dose of the compounds described herein being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, the dosage or the frequency of administration, or both, can be reduced, as a function of the symptoms, to a level at which the improved state of the disease, disorder or condition is maintained. Patients can, however, require intermittent treatment on a long-term basis upon any recurrence of symptoms.

The amount of a given agent that will correspond to such an amount will vary depending upon factors such as the particular compound, disease condition and its severity, the identity (e.g., age, weight, gender, etc.) of the subject or host in need of treatment, but can nevertheless be routinely determined in a manner known in the art according to the particular circumstances surrounding the case, including, e.g., the specific composition being administered, the route of administration, the condition being treated, and the subject or host being treated. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

Treatment regimens for depend on the individual and treatment being sought. In some embodiments, the composition is administered once a day, or twice a day, or three times a day, or four times a day, or five times a day, or six times a day. In alternate embodiments, the composition is administered every hour, or every 2 hours, or every 3 hours, or every four hours, or every 5 hours over the course of one day, or two days, or three days, or four days, or five days, or six days, or one week, or two weeks or three weeks, or one month.

In various embodiments, the composition is administered over the course of one day, two days, three days, four days, five days, six days, seven days, or every day for a week, two weeks, three weeks or four weeks. In other embodiments, the composition is administered over the course of a day for one month, two months, three months, four months, five months or six months. In specific embodiments, the treatment continues for 5 to 7 days, but may continue as needed.

In various embodiments, the composition is stored at room temperature to retain the activity of the enzymes and fining agents.

When administering the composition to an adolescent, the dose administered is based on the criteria shown in Table 1A below:

TABLE 1A

| Cancer Stage | Dose* |
| --- | --- |
| 0 to I | Low |
| II to III | Medium* |
| IV | High* |

When administering the composition to an adult, the dose administered is based on the criteria shown in Table 1B below:

TABLE 1B

| Cancer Stage | Dose* |
| --- | --- |
| 0 to I | Low to Medium* |
| II to III | Medium to High* |
| IV | High |

*Dosages in Table 1A and Table 1B are described in the Examples 38 and 39, infra. Low dosages can be injected into the vein, but medium and high dosages must be administered via drip (intravenous infusion) over several hours.

Having now generally described the invention, the same will be more readily understood through reference to the following examples which are provided by way of illustration, and are not intended to be limiting of the present invention, unless specified.

EXAMPLES

Example 1

Pineapple from Theory Values

Using a 5 mL graduated pipette to dilute 3 drops of freshly grated pineapple juice (from a mortar and pestle) into 12.0 mL of $H_2O$.

12.0 mL=3 times (3×) the amount of 100 drops (100 parts) used for experimentation. 100 drops=4.0 mL
5 mL capacity graduated pipette=25 drops/mL
25 drops/mL=0.04 mL per drop Drops of pineapple used×volume per drop=total volume of pineapple juice used for dilution. (3)×(0.04 mL)=0.12 mL Pineapple juice solute. Using the Percent Solution Equation (vol/vol %):

$$\frac{\text{volume}}{\text{volume}}\% = \frac{\text{volume of solute}}{\text{volume of solution}} \times 100$$

$$\text{vol/vol }\% = \frac{0.12 \text{ mL pineapple}}{12.0 \text{ mL H}_2\text{O}} \times 100$$

$$\text{vol/vol }\% = 1$$

Fresh pineapple juice stock solution=1% in 12.0 mL of $H_2O$. 1 drop of the pineapple stock solution is then added to 4.0 mL of $H_2O$ for experimentation. Using the Dilution formula $C_1V_1=C_2V_2$:

$$C_1V_1 = C_2V_2$$

$C_1$ = Starting concentration
$V_1$ = Starting volume
$C_2$ = Final concentration
$V_2$ = Final volume
$C_1$ = 1%
$V_1$ = .04 mL
$C_2$ = X
$V_2$ = 4.0 mL $$(.01) \times (.04) = X (4.0)$$
$$\frac{.0004}{4.0} = X$$
$$.0001 = X$$

Theoretical Results: 0.0001% final pineapple juice concentration.

Example 2

Pineapple Experimental Values

Using a 5 mL graduated pipette to dilute 3 drops of freshly grated pineapple juice (from a mortar and pestle) into 13.2 mL of $H_2O$.

13.2 mL=3 times (3×) the amount of 100 drops (100 parts) used for experimentation. 100 drops=4.4 mL 5 mL capacity graduated pipette=22.7 drops/mL 22.7 drops/mL=0.044 mL per drop Drops of pineapple used×volume per drop=total volume of pineapple juice used for dilution. (3)×(0.044 mL)=0.132 mL Pineapple juice solute. Using the Percent Solution Equation (vol/vol %):

$$\frac{\text{Volume}}{\text{Volume}}\% = \frac{\text{volume of solute}}{\text{volume of solution}} \times 100$$

$$\text{Vol/vol }\% = \frac{0.132 \text{ mL pineapple}}{13.2 \text{ mL H}_2\text{O}} \times 100$$

$$\text{Vol/vol }\% = 1$$

Fresh pineapple juice stock solution=1% in 13.2 mL of $H_2O$. 1 drop of the pineapple stock solution is then added to 4.4 mL of $H_2O$ for experimentation. Using the Dilution formula $C_1V_1=C_2V_2$:

$$C_1V_1 = C_2V_2$$

$C_1$ = Starting concentration
$V_1$ = Starting volume
$C_2$ = Final concentration
$V_2$ = Final volume
$C_1$ = 1%
$V_1$ = .044 mL
$C_2$ = X
$V_2$ = 4.4 mL $$(.01) \times (.044) = X (4.4)$$
$$\frac{.00044}{4.4} = X$$
$$.0001 = X$$

Experimental Results: 0.0001% final pineapple juice concentration.

Example 3

Ginger Root from Theory Values

Using a 5 mL graduated pipette to dilute 3 drops of freshly grated ginger root (from a mortar and pestle) into 12.0 mL of $H_2O$.

12.0 mL=3 times (3×) the amount of 100 drops (100 parts) used for experimentation. 100 drops=4.0 mL 5 mL capacity graduated pipette=25 drops/mL 25 drops/mL=0.04 mL per drop Drops of ginger used×volume per drop=total volume of ginger root juice used for dilution. (3)×(0.04 mL)=0.12 mL ginger root juice solute. Using the Percent Solution Equation (vol/vol %):

$$\frac{\text{Volume}}{\text{Volume}}\% = \frac{\text{volume of solute}}{\text{volume of solution}} \times 100$$

$$\text{Vol/vol }\% = \frac{0.12 \text{ mL ginger}}{12.0 \text{ mL H}_2\text{O}} \times 100$$

$$\text{Vol/vol }\% = 1$$

Fresh ginger root juice stock solution=1% in 12.0 mL of $H_2O$. 1 drop of the ginger stock solution is then added to 4.0 mL of $H_2O$ for experimentation. Using the Dilution formula $C_1V_1=C_2V_2$:

$$C_1V_1 = C_2V_2$$

$C_1$ = Starting concentration
$V_1$ = Starting volume
$C_2$ = Final concentration
$V_2$ = Final volume
$C_1$ = 1%
$V_1$ = .04 mL
$C_2$ = X
$V_2$ = 4.0 mL $$(.01) \times (.04) = X (4.0)$$
$$\frac{.0004}{4.0} = X$$
$$.0001 = X$$

Theoretical Results: 0.0001% final ginger root juice concentration for experimentation.

Example 4

Ginger Root Experimental Values

Using a 5 mL graduated pipette to dilute 3 drops of freshly grated ginger root juice (from a mortar and pestle) into 13.2 mL of $H_2O$.

13.2 mL=3 times (3×) the amount of 100 drops (100 parts) used for experimentation. 100 drops=4.4 mL
5 mL capacity graduated pipette=22.7 drops/mL
22.7 drops/mL=0.044 mL per drop Drops of ginger root juice used×volume per drop=total volume of ginger root juice used for dilution. (3)×(0.044 mL)=0.132 mL Ginger root juice solute. Using the Percent Solution Equation (vol/vol %):

$$\frac{\text{Volume}}{\text{Volume}}\% = \frac{\text{volume of solute}}{\text{volume of solution}} \times 100$$

$$\text{Vol/vol \%} = \frac{0.132 \text{ mL ginger}}{13.2 \text{ mL } H_2O} \times 100$$

$$\text{Vol/vol \%} = 1$$

Fresh ginger root juice stock solution=1% in 13.2 mL of $H_2O$. 1 drop of the ginger stock solution is then added to 4.4 mL of $H_2O$ for experimentation. Using the Dilution formula $C_1V_1=C_2V_2$:

$$C_1V_1 = C_2V_2$$

$C_1$ = Starting concentration
$V_1$ = Starting volume
$C_2$ = Final concentration
$V_2$ = Final volume
$C_1$ = 1%
$V_1$ = .044 mL
$C_2$ = X
$V_2$ = 4.4 mL (.01) × (.044) = X (4.4)
.00044 = X
4.4
.0001 = X Experimental Results: 0.0001% final ginger root juice concentration

Example 5

Egg White from Theory Values

Using a 5 mL graduated pipette to dilute 2 drops of freshly grated pineapple juice (from a mortar and pestle) into 12.0 mL of $H_2O$.

12.0 mL=3 times (3×) the amount of 100 drops (100 parts) used for experimentation. 100 drops=4.0 mL
5 mL capacity graduated pipette=25 drops/mL
25 drops/mL=0.04 mL per drop Drops of egg white used×volume per drop=total volume of egg white used for dilution. (2)×(0.04 mL)=0.8 mL egg white solute. Using the Percent Solution Equation (vol/vol %):

$$\frac{\text{Volume}}{\text{Volume}}\% = \frac{\text{volume of solute}}{\text{volume of solution}} \times 100$$

$$\text{Vol/vol \%} = \frac{0.8 \text{ mL egg white}}{12.0 \text{ mL } H_2O} \times 100$$

$$\text{Vol/vol \%} = .67$$

Fresh egg white stock solution=0.67% in 12.0 mL of $H_2O$ 1 drop of the egg white stock solution is then added to 4.0 mL of $H_2O$ for experimentation. Using the Dilution formula $C_1V_1=C_2V_2$:

$$C_1V_1 = C_2V_2$$

$C_1$ = Starting concentration
$V_1$ = Starting volume
$C_2$ = Final concentration
$V_2$ = Final volume
$C_1$ = 0.67%
$V_1$ = .04 mL
$C_2$ = X
$V_2$ = 4.0 mL (.0067) × (.04) = X (4.0)
.000268 = X
4.0
.000067 = X Theoretical Results: 0.000067% final egg white concentration.

Example 6

Egg White Experimental Values

Using a 5 mL graduated pipette to dilute 2 drops of fresh egg white (from a mortar and pestle) into 13.2 mL of $H_2O$.

13.2 mL=3 times (3×) the amount of 100 drops (100 parts) used for experimentation. 100 drops=4.4 mL
5 mL capacity graduated pipette=22.7 drops/mL
22.7 drops/mL=0.044 mL per drop Drops of pineapple used×volume per drop=total volume of egg white used for dilution. (2)×(0.044 mL)=0.088 mL Egg white solute. Using the Percent Solution Equation (vol/vol %):

$$\frac{\text{Volume}}{\text{Volume}}\% = \frac{\text{volume of solute}}{\text{volume of solution}} \times 100$$

$$\text{Vol/vol \%} = \frac{0.088 \text{ mL egg white}}{13.2 \text{ mL } H_2O} \times 100$$

$$\text{Vol/vol \%} = 0.67$$

Fresh egg white stock solution=0.67% in 13.2 mL of $H_2O$. 1 drop of the egg white solution is then added to 4.4 mL of $H_2O$ for experimentation. Using the Dilution formula $C_1V_1=C_2V_2$:

$$C_1V_1 = C_2V_2$$

$C_1$ = Starting concentration
$V_1$ = Starting volume
$C_2$ = Final concentration
$V_2$ = Final volume
$C_1$ = 0.67%
$V_1$ = .044 mL
$C_2$ = X
$V_2$ = 4.4 mL -continued
$$(.0067) \times (.044) = X (4.4)$$
$$.00029 = X$$
$$\frac{4.4}{.000067} = X$$

Experimental Results: 0.000067% final egg white concentration.

Example 7

Kiwi Juice Experimental Values

Using a 3 mL graduated pipette to dilute 2 drops of freshly grated kiwi juice (from a mortar and pestle) into 4.0 mL of $H_2O$.
  100 drops (100 parts) used for experimentation. 100 drops=4.0 mL
  3 mL capacity graduated pipette=25 drops/mL
  25 drops/mL=0.04 mL per drop
  Drops of kiwi used×volume per drop=total volume of kiwi juice used for dilution. (2)×(0.04 mL)=0.08 mL Kiwi juice solute. Using the Percent Solution Equation (vol/vol %):

$$\frac{volume}{volume}\% = \frac{volume\ of\ solute}{volume\ of\ solution} \times 100$$
$$vol/vol\% = \frac{0.08\ mL\ pineapple}{4.0\ mL\ H_2O} \times 100$$
$$vol/vol\% = 2$$

Example 8

Exemplary Fresh Kiwi Juice Stock Solution—Concentration #2 (Moderate)

*Fresh kiwi juice stock solution was tested before dilution
Using a 3 mL graduated pipette to dilute 5 drops of freshly grated kiwi juice (from a mortar and pestle) into 16.0 mL of $H_2O$.
  16.0 mL=4 times (4×) the amount of 100 drops (100 parts) used for experimentation. 100 drops=4.0 mL
  3 mL capacity graduated pipette=25 drops/mL
  25 drops/mL=0.04 mL per drop
  Drops of kiwi used×volume per drop=total volume of kiwi juice used for dilution. (5)×(0.04 mL)=0.2 mL Kiwi juice solute. [Using the Percent Solution Equation (vol/vol %)]

$$\frac{volume}{volume}\% = \frac{volume\ of\ solute}{volume\ of\ solution} \times 100$$
$$vol/vol\% = \frac{0.2\ mL\ kiwi}{16.0\ mL\ H_2O} \times 100$$
$$vol/vol\% = 1.25$$

Fresh kiwi juice stock solution=1.25% in 16.0 mL of $H_2o$. 1 drop of the kiwi stock solution is then added to 4.0 mL of $H_2O$ for experimentation. [Using the Dilution formula $C_1V_1=C_2V_2$]

$$C_1V_1 = C_2V_2$$
$C_1$ = Starting concentration
$V_1$ = Starting volume
$C_2$ = Final concentration
$V_2$ = Final volume
$C_1$ = 1.25%
$V_1$ = .04 mL
$C_2$ = X
$V_2$ = 4.0 mL $$(.0125) \times (.04) = X (4.0)$$
$$\frac{.0005}{4.0} = X$$
$$.000125 = X$$

0.000125% final kiwi juice concentration for experimentation

Example 9

Kiwiberry Juice Experimental Values—Concentration #1 (Strong)

Using a 3 mL graduated pipette to dilute 2 drops of freshly grated kiwiberry (with skins on) juice (from a mortar and pestle) into 4.0 mL of $H_2O$.
  100 drops (100 parts) used for experimentation. 100 drops=4.0 mL
  3 mL capacity graduated pipette=25 drops/mL
  25 drops/mL=0.04 mL per drop
  Drops of kiwiberry used×volume per drop=total volume of kiwiberry juice used for dilution. (2)×(0.04 mL)=0.08 mL Kiwiberry juice solute. [Using the Percent Solution Equation (vol/vol %)]

$$\frac{volume}{volume}\% = \frac{volume\ of\ solute}{volume\ of\ solution} \times 100$$
$$vol/vol\% = \frac{0.08\ mL\ kiwiberry}{4.0\ mL\ H_2O} \times 100$$
$$vol/vol\% = 2$$

Example 10

Exemplary Fresh Kiwiberry Juice Stock Solution—Concentration #2 (Moderate)

*Fresh kiwiberry juice stock solution was tested before dilution
Diluted Kiwiberry:
Using a 3 mL graduated pipette to dilute 3 drops of freshly grated kiwiberry (with skins on) juice (from a mortar and pestle) into 8.0 mL of $H_2O$.
  8.0 mL=2 times (2×) the amount of 100 drops (100 parts) used for experimentation. 100 drops=4.0 mL
  3 mL capacity graduated pipette=25 drops/mL
  25 drops/mL=0.04 mL per drop
  Drops of kiwiberry used×volume per drop=total volume of kiwiberry juice used for dilution. (3)×(0.04 mL)=0.12 mL Kiwiberry juice solute [Using the Percent Solution Equation (vol/vol %)]

$$\frac{volume}{volume}\% = \frac{volume\ of\ solute}{volume\ of\ solution} \times 100$$

$$\text{vol/vol}\% = \frac{0.12 \text{ mL kiwiberry}}{8.0 \text{ mL H}_2\text{O}} \times 100$$

$$\text{vol/vol}\% = 1.5$$

Fresh kiwiberry juice stock solution=1.5% in 8.0 mL of $H_2O$ 1 drop of the kiwiberry stock solution is then added to 4.0 mL of $H_2O$ for experimentation. [Using the Dilution formula $C_1V_1=C_2V_2$]

$$C_1V_1 = C_2V_2$$

$C_1$ = Starting concentration
$V_1$ = Starting volume
$C_2$ = Final concentration
$V_2$ = Final volume
$C_1$ = 1.5%
$V_1$ = .04 mL
$C_2$ = X
$V_2$ = 4.0 mL $$(.015) \times (.04) = X (4.0)$$
$$\frac{.0006}{4.0} = X$$
$$.00015 = X$$

0.00015% final kiwiberry juice concentration for experimentation

Example 11

Mango Juice Experimental Values—Concentration #1 (Strong)

Using a 3 mL graduated pipette to dilute 2 drops of freshly grated mango juice (from a mortar and pestle) into 4.0 mL of $H_2O$.

100 drops (100 parts) used for experimentation. 100 drops=4.0 mL
3 mL capacity graduated pipette=25 drops/mL
25 drops/mL=0.04 mL per drop
Drops of mango used×volume per drop=total volume of mango juice used for dilution. (2)×(0.04 mL)=0.08 mL Mango juice solute. [Using the Percent Solution Equation (vol/vol %)]

$$\frac{\text{volume}}{\text{volume}}\% = \frac{\text{volume of solute}}{\text{volume of solution}} \times 100$$

$$\text{vol/vol}\% = \frac{0.08 \text{ mL mango}}{4.0 \text{ mL H}_2\text{O}} \times 100$$

$$\text{vol/vol}\% = 2$$

Example 12

Exemplary Fresh Mango Juice Stock Solution—Concentration #2 (Moderate)

*Fresh mango juice stock solution was tested before dilution

Diluted mango: Using a 3 mL graduated pipette to dilute 3 drops of freshly grated mango juice (from a mortar and pestle) into 8.0 mL of $H_2O$.

8.0 mL=2 times (2×) the amount of 100 drops (100 parts) used for experimentation. 100 drops=4.0 mL
3 mL capacity graduated pipette=25 drops/mL
25 drops/mL=0.04 mL per drop
Drops of mango used×volume per drop=total volume of mango juice used for dilution. (3)×(0.04 mL)=0.12 mL Mango juice solute. [Using the Percent Solution Equation (vol/vol %)]

$$\frac{\text{volume}}{\text{volume}}\% = \frac{\text{volume of solute}}{\text{volume of solution}} \times 100$$

$$\text{vol/vol}\% = \frac{0.12 \text{ mL mango}}{8.0 \text{ mL H}_2\text{O}} \times 100$$

$$\text{vol/vol}\% = 1.5$$

Fresh mango juice stock solution=1.5% in 8.0 mL of $H_2O$ 1 drop of the mango stock solution is then added to 4.0 mL of $H_2O$ for experimentation. [Using the Dilution formula $C_1V_1=C_2V_2$]

$$C_1V_1 = C_2V_2$$

$C_1$ = Starting concentration
$V_1$ = Starting volume
$C_2$ = Final concentration
$V_2$ = Final volume
$C_1$ = 1.5%
$V_1$ = .04 mL
$C_2$ = X
$V_2$ = 4.0 mL $$(.015) \times (.04) = X (4.0)$$
$$\frac{.0006}{4.0} = X$$
$$.00015 = X$$

0.00015% final mango juice concentration for experimentation

Example 13

Banana Juice Experimental Values—Concentration #1 (Strong)

Using a 3 mL graduated pipette to dilute 2 drops of freshly grated banana (with skins/peel on) juice (from a mortar and pestle) into 4.0 mL of $H_2O$.

100 drops (100 parts) used for experimentation. 100 drops=4.0 mL
3 mL capacity graduated pipette=25 drops/mL
25 drops/mL=0.04 mL per drop
Drops of banana used×volume per drop=total volume of banana juice used for dilution. (2)×(0.04 mL)=0.08 mL Banana juice solute. [Using the Percent Solution Equation (vol/vol %)]

$$\frac{\text{volume}}{\text{volume}}\% = \frac{\text{volume of solute}}{\text{volume of solution}} \times 100$$

$$\text{vol/vol}\% = \frac{0.08 \text{ mL banana}}{4.0 \text{ mL H}_2\text{O}} \times 100$$

$$\text{vol/vol}\% = 2$$

Example 14

Exemplary Fresh Banana Juice Stock Solution—Concentration #2 (Moderate)

*Fresh banana juice stock solution was tested before dilution

Diluted Banana:

Using a 3 mL graduated pipette to dilute 4 drops of freshly grated banana (with skins/peel on) juice (from a mortar and pestle) into 8.0 mL of $H_2O$.

8.0 mL=2 times (2×) the amount of 100 drops (100 parts) used for experimentation. 100 drops=4.0 mL 3 mL capacity graduated pipette=25 drops/mL 25 drops/mL=0.04 mL per drop Drops of banana used×volume per drop=total volume of banana juice used for dilution. (4)×(0.04 mL)=0.16 mL Banana juice solute [Using the Percent Solution Equation (vol/vol %)]

$$\frac{\text{volume}}{\text{volume}}\% = \frac{\text{volume of solute}}{\text{volume of solution}} \times 100$$

$$\text{vol/vol}\% = \frac{0.16 \text{ mL banana}}{8.0 \text{ mL } H_2O} \times 100$$

$$\text{vol/vol}\% = 2$$

Fresh banana juice stock solution=2% in 8.0 mL of $H_2O$. 1 drop of the banana stock solution is then added to 4.0 mL of $H_2O$ for experimentation. [Using the Dilution formula $C_1V_1=C_2V_2$]

$$C_1V_1 = C_2V_2$$

$C_1$ = Starting concentration
$V_1$ = Starting volume
$C_2$ = Final concentration
$V_2$ = Final volume
$C_1$ = 2%
$V_1$ = .04 mL
$C_2$ = X
$V_2$ = 4.0 mL (.02) × (.04) = X (4.0)
.0008 = X
 4.0
.0002 = X 0.0002% final banana, juice concentration for experimentation

Example 15

Turmeric Experimental Values—Concentration #1 (Moderate)

Using a 3 mL graduated pipette to dilute 2 drops of freshly grated turmeric juice (from a mortar and pestle) into 4.0 mL of $H_2O$.

100 drops (100 parts) used for experimentation. 100 drops=4.0 mL 3 mL capacity graduated pipette=25 drops/mL 25 drops/mL=0.04 mL per drop Drops of turmeric used×volume per drop=total volume of turmeric juice used for dilution. (2)×(0.04 mL)=0.08 mL Turmeric juice solute [Using the Percent Solution Equation (vol/vol %)]

$$\frac{\text{volume}}{\text{volume}}\% = \frac{\text{volume of solute}}{\text{volume of solution}} \times 100$$

$$\text{vol/vol}\% = \frac{0.08 \text{ mL banana}}{4.0 \text{ mL } H_2O} \times 100$$

$$\text{vol/vol}\% = 2$$

Example 16

Exemplary Turmeric Stock Solution—Concentration #2 (Strong)

*Fresh turmeric juice stock solution was tested

Using a 3 mL graduated pipette to dilute 3 drops of freshly grated turmeric juice (from a mortar and pestle) into 4.0 mL of $H_2O$.

100 drops (100 parts) used for experimentation. 100 drops=4.0 mL 3 mL capacity graduated pipette=25 drops/mL 25 drops/mL=0.04 mL per drop Drops of turmeric used×volume per drop=total volume of turmeric juice used for dilution. (3)×(0.04 mL)=0.12 mL Turmeric juice solute [Using the Percent Solution Equation (vol/vol %)]

$$\frac{\text{volume}}{\text{volume}}\% = \frac{\text{volume of solute}}{\text{volume of solution}} \times 100$$

$$\text{vol/vol}\% = \frac{0.12 \text{ mL turmeric}}{4.0 \text{ mL } H_2O} \times 100$$

$$\text{vol/vol}\% = 3$$

Example 17

Fresh Papaya Juice Experimental Values—Concentration #1 (Very Strong)

*Fresh papaya juice stock solution was tested before dilution

Using a 3 mL graduated pipette to dilute 1 drop of freshly grated papaya juice (from a mortar and pestle) into 4.0 mL of $H_2O$.

100 drops (100 parts) used for experimentation. 100 drops=4.0 mL 3 mL capacity graduated pipette=25 drops/mL 25 drops/mL=0.04 mL per drop Drops of papaya used×volume per drop=total volume of papaya juice used for dilution. (1)×(0.04 mL)=0.04 mL Papaya juice solute [Using the Percent Solution Equation (vol/vol %)]

$$\frac{\text{volume}}{\text{volume}}\% = \frac{\text{volume of solute}}{\text{volume of solution}} \times 100$$

$$\text{vol/vol}\% = \frac{0.04 \text{ mL papaya}}{4.0 \text{ mL } H_2O} \times 100$$

$$\text{vol/vol}\% = 1$$

Example 18

Fresh Papaya Juice Experimental
Values—Concentration #2 (Strong)

*Fresh papaya juice stock solution was tested before dilution

Using a 3 mL graduated pipette to dilute 2 drops of freshly grated papaya juice (from a mortar and pestle) into 4.0 mL of $H_2O$.

100 drops (100 parts) used for experimentation. 100 drops=4.0 mL 3 mL capacity graduated pipette=25 drops/mL 25 drops/mL=0.04 mL per drop Drops of papaya used×volume per drop=total volume of papaya juice used for dilution. (2)×(0.04 mL)=0.08 mL Papaya juice solute [Using the Percent Solution Equation (vol/vol %)]

$$\frac{volume}{volume}\% = \frac{volume\ of\ solute}{volume\ of\ solution} \times 100$$

$$vol/vol\% = \frac{0.08\ mL\ papaya}{4.0\ mL\ H_2O} \times 100$$

$$vol/vol\% = 2$$

Example 19

Fresh Papaya Juice Experimental
Values—Concentration #3 (Moderate)

Diluted Papaya:

Using a 3 mL graduated pipette to dilute 3 drops of freshly grated papaya juice (from a mortar and pestle) into 12.0 mL of $H_2O$.

12.0 mL=3 times (3×) the amount of 100 drops (100 parts) used for experimentation. 100 drops=4.0 mL 3 mL capacity graduated pipette=25 drops/mL 25 drops/mL=0.04 mL per drop Drops of papaya used×volume per drop=total volume of papaya juice used for dilution. (3)×(0.04 mL)=0.12 mL Banana juice solute [Using the Percent Solution Equation (vol/vol %)]

$$\frac{volume}{volume}\% = \frac{volume\ of\ solute}{volume\ of\ solution} \times 100$$

$$vol/vol\% = \frac{0.12\ mL\ banana}{12.0\ mL\ H_2O} \times 100$$

$$vol/vol\% = 1$$

Fresh papaya juice stock solution=1% in 12.0 mL of $H_2O$ 1 drop of the papaya stock solution is then added to 4.0 mL of $H_2O$ for experimentation. [Using the Dilution formula $C_1V_1 = C_2V_2$]

$$C_1V_1 = C_2V_2$$

$C_1$ = Starting concentration
$V_1$ = Starting volume
$C_2$ = Final concentration
$V_2$ = Final volume
$C_1$ = 1%
$V_1$ = .04 mL
$C_2$ = X
$V_2$ = 4.0 mL $(.01) \times (.04) = X (4.0)$
$.0004 = X$
$\overline{4.0}$
$.0001 = X$ 0.0001% final papaya juice concentration for experimentation

Example 20

Fresh Papaya Juice Experimental
Values—Concentration #4 (Slow Acting)

Diluted Papaya:

Using a 3 mL graduated pipette to dilute 4 drops of freshly grated papaya juice (from a mortar and pestle) into 12.0 mL of $H_2O$.

12.0 mL=3 times (3×) the amount of 100 drops (100 parts) used for experimentation. 100 drops=4.0 mL 3 mL capacity graduated pipette=25 drops/mL 25 drops/mL=0.04 mL per drop Drops of papaya used×volume per drop=total volume of papaya juice used for dilution. (4)×(0.04 mL)=0.16 mL Papaya juice solute [Using the Percent Solution Equation (vol/vol %)]

$$\frac{volume}{volume}\% = \frac{volume\ of\ solute}{volume\ of\ solution} \times 100$$

$$vol/vol\% = \frac{0.16\ mL\ papaya}{12.0\ mL\ H_2O} \times 100$$

$$vol/vol\% = 1.3$$

Fresh papaya juice stock solution=1.3% in 12.0 mL of $H_2O$. 1 drop of the papaya stock solution is then added to 4.0 mL of $H_2O$ for experimentation. [Using the Dilution formula $C_1V_1 = C_2V_2$]

$$C_1V_1 = C_2V_2$$

$C_1$ = Starting concentration
$V_1$ = Starting volume
$C_2$ = Final concentration
$V_2$ = Final volume
$C_1$ = 1.3%
$V_1$ = .04 mL
$C_2$ = X
$V_2$ = 4.0 mL $(.013) \times (.04) = X (4.0)$
$.00053 = X$
$\overline{4.0}$
$.00013 = X$ 0.00013% final papaya juice concentration for experimentation

Example 21

Exemplary Combined Enzymes—Ginger+Turmeric Experimental Values—Concentration #1 (Very Strong)

*Fresh ginger and turmeric juice stock solution was tested before dilution.

Using a 3 mL graduated pipette to dilute 1 drop each of freshly grated ginger and turmeric juice (from a mortar and pestle) into 4.0 mL of $H_2O$.

- 100 drops (100 parts) used for experimentation. 100 drops=4.0 mL
- 3 mL capacity graduated pipette=25 drops/mL
- 25 drops/mL=0.04 mL per drop Drops of (ginger+turmeric) used×volume per drop=total volume of ginger & turmeric juice used for dilution. (2)×(0.04 mL)=0.08 mL Ginger and Turmeric juice solute [Using the Percent Solution Equation (vol/vol %)]

$$\frac{volume}{volume}\% = \frac{volume\ of\ solute}{volume\ of\ solution} \times 100$$

$$vol/vol\ \% = \frac{0.08\ mL\ ginger\ \&\ tumeric}{4.0\ mL\ H_2O} \times 100$$

$$vol/vol\ \% = 2$$

Fresh ginger and turmeric juice stock solution=2% in 4.0 mL of $H_2O$ (* 1% of fresh ginger+1% fresh turmeric=2%)

Example 22

Exemplary Combined Enzymes—Ginger+Turmeric Experimental Values—Concentration #2 (Moderate)

Diluted Ginger+Non-Diluted Turmeric:

Using a 3 mL graduated pipette to dilute 3 drops of freshly grated ginger juice (from a mortar and pestle) into 12.0 mL of $H_2O$.

- 12.0 mL=3 times (3×) the amount of 100 drops (100 parts) used for experimentation. 100 drops=4.0 mL
- 3 mL capacity graduated pipette=25 drops/mL
- 25 drops/mL=0.04 mL per drop Drops of ginger used×volume per drop=total volume of ginger juice used for dilution.

(3)×(0.04 mL)=0.12 mL Ginger juice solute [Using the Percent Solution Equation (vol/vol %)]

$$\frac{volume}{volume}\% = \frac{volume\ of\ solute}{volume\ of\ solution} \times 100$$

$$vol/vol\ \% = \frac{0.12\ mL\ ginger}{12.0\ mL\ H_2O} \times 100$$

$$vol/vol\ \% = 1$$

Fresh ginger juice stock solution=1% in 12.0 mL of $H_2O$. 1 drop of the ginger stock solution is then added to 4.0 mL of $H_2O$ for experimentation. [Using the Dilution formula $C_1V_1=C_2V_2$]

$$C_1V_1 = C_2V_2$$

$C_1$ = Starting concentration
$V_1$ = Starting volume
$C_2$ = Final concentration
$V_2$ = Final volume
$C_1$ = 1%
$V_1$ = .04 mL
$C_2$ = X
$V_2$ = 4.0 mL $$(.01) \times (.04) = X (4.0)$$
$$\frac{.0004}{4.0} = X$$
$$.0001 = X$$

0.0001% final ginger juice concentration for experimentation

Using a 3 mL graduated pipette to dilute 1 drop of freshly grated turmeric juice (from a mortar and pestle) into 4.0 mL of $H_2O$.

- 100 drops (100 parts) used for experimentation. 100 drops=4.0 mL
- 3 mL capacity graduated pipette=25 drops/mL
- 25 drops/mL=0.04 mL per drop Drops of turmeric used×volume per drop=total volume of turmeric juice used for dilution. (1)×(0.04 mL)=0.04 mL Turmeric juice solute [Using the Percent Solution Equation (vol/vol %)]

$$\frac{volume}{volume}\% = \frac{volume\ of\ solute}{volume\ of\ solution} \times 100$$

$$vol/vol\ \% = \frac{0.04\ mL\ tumeric}{4.0\ mL\ H_2O} \times 100$$

$$vol/vol\ \% = 2$$

Fresh turmeric juice stock solution=1% in 4.0 mL of $H_2O$
Final Ginger+Turmeric juice concentration=1% turmeric+0.0001% ginger=1.001% combined ginger+turmeric juice in 4.0 mL $H_2O$

Example 23

Isinglass Fining Agent Experimental Values—Concentration #1 (Fast-Moderate to Slightly Strong)

Using a 3 mL graduated pipette to dilute 2 drops of isinglass into 4.0 mL of $H_2O$.

- 100 drops (100 parts) used for experimentation. 100 drops=4.0 mL
- 3 mL capacity graduated pipette=25 drops/mL
- 25 drops/mL=0.04 mL per drop Drops of isinglass used×volume per drop=total volume of isinglass used for dilution. (2)×(0.04 mL)=0.08 mL Isinglass solute [Using the Percent Solution Equation (vol/vol %)]

$$\frac{volume}{volume}\% = \frac{volume\ of\ solute}{volume\ of\ solution} \times 100$$

$$vol/vol\ \% = \frac{0.08\ mL\ isinglass}{4.0\ mL\ H_2O} \times 100$$

$$vol/vol\ \% = 2$$

Isinglass stock solution=2% in 4.0 mL of $H_2O$ for experimentation

Example 24

Kieselsol Fining Agent Experimental Values—Concentration #1 (Slow)

Using a 3 mL graduated pipette to dilute 2 drops of kieselsol into 4.0 mL of $H_2O$.
- 100 drops (100 parts) used for experimentation. 100 drops=4.0 mL
- 3 mL capacity graduated pipette=25 drops/mL
- 25 drops/mL=0.04 mL per drop Drops of kieselsol used×volume per drop=total volume of kieselsol used for dilution. (2)×(0.04 mL)=0.08 mL Kieselsol solute [Using the Percent Solution Equation (vol/vol %)]

$$\frac{volume}{volume}\% = \frac{volume\ of\ solute}{volume\ of\ solution} \times 100$$

$$vol/vol\ \% = \frac{0.08\ mL\ kieselsol}{4.0\ mL\ H_2O} \times 100$$

$$vol/vol\ \% = 2$$

Kieselsol stock solution=2% in 4.0 mL of $H_2O$ for experimentation

Example 25

Chitosan Fining Agent Experimental Values—Concentration #1 (Slow)

Using a 3 mL graduated pipette to dilute 1 drop of chitosan into 4.0 mL of $H_2O$.
- 100 drops (100 parts) used for experimentation. 100 drops=4.0 mL
- 3 mL capacity graduated pipette=25 drops/mL
- 25 drops/mL=0.04 mL per drop Drops of chitosan used×volume per drop=total volume of chitosan used for dilution. (1)×(0.04 mL)=0.04 mL Chitosan solute [Using the Percent Solution Equation (vol/vol %)]

$$\frac{volume}{volume}\% = \frac{volume\ of\ solute}{volume\ of\ solution} \times 100$$

$$vol/vol\ \% = \frac{0.04\ mL\ chitosan}{4.0\ mL\ H_2O} \times 100$$

$$vol/vol\ \% = 1$$

Chitosan stock solution=1% in 4.0 mL of $H_2O$ for experimentation

Example 26

Chitosan Fining Agent Experimental Values—Concentration #3 (Moderately Fast)

Dilute Chitosan (based on package instructions) Per package instructions: 2 fluid ounce of chitosan needs to be diluted into 30 mL of warm $H_2O$.

$$1\ fl\ oz = 29.57\ mL$$

$$\frac{59.14\ mL\ chitosan}{30\ mL\ H_2O} = \frac{x}{12\ mL\ H_2O}$$

$$x = 23.65\ mL\ chitosan\ needed\ for\ 12\ mL\ H_2O\ for\ experimentation$$

Using a 3 mL graduated pipette to dilute 591.25 drops of chitosan into 12.0 mL of $H_2O$.
- 12.0 mL=3 times (3×) the amount of 100 drops (100 parts) used for experimentation. 100 drops=4.0 mL
- 3 mL capacity graduated pipette=25 drops/mL
- 25 drops/mL=0.04 mL per drop Drops of chitosan used×volume per drop=total volume of chitosan used for dilution. (591.25)×(0.04 mL)=23.65 mL Chitosan solute [Using the Percent Solution Equation (vol/vol %)]

$$\frac{volume}{volume}\% = \frac{volume\ of\ solute}{volume\ of\ solution} \times 100$$

$$vol/vol\ \% = \frac{23.65\ mL\ chitosan}{12.0\ mL\ H_2O} \times 100$$

$$vol/vol\ \% = 197$$

Dilute Chitosan stock solution=197% in 12.0 mL of $H_2O$ for experimentation. 1 drop of the chitosan dilute stock solution is then added to 4.0 mL of $H_2O$ for experimentation. [Using the Dilution formula $C_1V_1=C_2V_2$]

$$C_1V_1 = C_2V_2$$

$C_1$ = Starting concentration
$V_1$ = Starting volume
$C_2$ = Final concentration
$V_2$ = Final volume
$C_1$ = 197%
$V_1$ = .04 mL
$C_2$ = X
$V_2$ = 4.0 mL $$(1.97) \times (.04) = X\ (4.0)$$
$$\frac{.0776}{4.0} = X$$
$$.0194 = X$$

0.0194% final chitosan concentration for experimentation

Example 27

Combined Kieselsol+Chitosan Fining Agent Experimental Values—Concentration #1 (Fast)

Using a 3 mL graduated pipette to dilute 1 drop each of undiluted kieselsol and chitosan into 4.0 mL of $H_2O$.
- 100 drops (100 parts) used for experimentation. 100 drops=4.0 mL
- 3 mL capacity graduated pipette=25 drops/mL
- 25 drops/mL=0.04 mL per drop Drops of kieselsol and chitosan used×volume per drop=total volume of kieselsol and chitosan used for dilution. (2)×(0.04 mL)=0.08 mL Kieselsol and Chitosan solute. [Using the Percent Solution Equation (vol/vol %)]

$$\frac{volume}{volume}\% = \frac{volume\ of\ solute}{volume\ of\ solution} \times 100$$

-continued $$\text{vol/vol } \% = \frac{0.08 \text{ mL kieselsol}}{4.0 \text{ mL H}_2\text{O}} \times 100$$

$$\text{vol/vol } \% = 2$$

Example 28

Combined Kieselsol+Chitosan Stock Solution—Concentration #2 (Slow)

Using a 3 mL graduated pipette to dilute 1 drop of undiluted kieselsol into 4.0 mL of $H_2O$.
- 100 drops (100 parts) used for experimentation. 100 drops=4.0 mL
- 3 mL capacity graduated pipette=25 drops/mL
- 25 drops/mL=0.04 mL per drop Drops of kieselsol used×volume per drop=total volume of kieselsol used for dilution. (1)×(0.04 mL)=0.04 mL Kieselsol solute [Using the Percent Solution Equation (vol/vol %)]

$$\frac{\text{volume}}{\text{volume}}\% = \frac{\text{volume of solute}}{\text{volume of solution}} \times 100$$

$$\text{vol/vol } \% = \frac{0.04 \text{ mL kieselsol}}{4.0 \text{ mL H}_2\text{O}} \times 100$$

$$\text{vol/vol } \% = 1$$

Kieselsol stock solution=1% in 4.0 mL of $H_2O$ for experimentation. 1 drop of the chitosan dilute stock solution is then added to 4.0 mL of $H_2O$ for experimentation. [Using the Dilution formula $C_1V_1=C_2V_2$]

$$C_1V_1 = C_2V_2$$

$C_1$ = Starting concentration
$V_1$ = Starting volume
$C_2$ = Final concentration
$V_2$ = Final volume
$C_1$ = 1.97%
$V_1$ = .04 mL
$C_2$ = X
$V_2$ = 4.0 mL (1.97) × (.04) = X (4.0)
.0776 = X
  4.0
.0194 = X 0.0194% final chitosan concentration for experimentation
Final kieselsol chitosan concentration=1.0194% in 4.0 mL of $H_2O$ for experimentation.

Example 29

Sodium Alginate Fining Agent Experimental Values—Concentration #1 (Fast)

1:100 dilution. Using a 3 mL graduated pipette to dilute 0.12 g undiluted sodium alginate into 12.0 mL of $H_2O$.
- 12.0 mL=3 times (3×) the amount of 100 drops (100 parts) used for experimentation. 100 drops=4.0 mL
- 3 mL capacity graduated pipette=25 drops/mL
- 25 drops/mL=0.04 mL per drop Per Package instructions=2 grams of sodium alginate per 200 mL of $H_2O$. [Using the Percent Solution Equation (weight/vol %)]

$$\frac{\text{weight}}{\text{volume}}\% = \frac{\text{weight of solute}}{\text{volume of solution}} \times 100$$

$$\text{w/vol } \% = \frac{0.12 \text{ grams sodium alginate}}{12.0 \text{ mL H}_2\text{O}} \times 100$$

$$\text{w/vol } \% = 1$$

Sodium Alginate stock solution=1% in 12.0 mL of $H_2O$ for experimentation

Example 30

Sodium Alginate Fining Agent Experimental Values—Concentration #2 (Slow)

1:50 dilution. Using a 3 mL graduated pipette to dilute 0.24 g undiluted sodium alginate into 12.0 mL of $H_2O$.
- 12.0 mL=3 times (3×) the amount of 100 drops (100 parts) used for experimentation. 100 drops=4.0 mL
- 3 mL capacity graduated pipette=25 drops/mL
- 25 drops/mL=0.04 mL per drop Per Package instructions=2 grams of sodium alginate per 200 mL of $H_2O$. [Using the Percent Solution Equation (weight/vol %)]

$$\frac{\text{weight}}{\text{volume}}\% = \frac{\text{weight of solute}}{\text{volume of solution}} \times 100$$

$$\text{w/vol } \% = \frac{0.24 \text{ grams sodium alginate}}{12.0 \text{ mL H}_2\text{O}} \times 100$$

$$\text{w/vol } \% = 2$$

Sodium Alginate stock solution=2% in 12.0 mL of $H_2O$ for experimentation

Example 31

Bentonite Fining Agent Experimental Values—Concentration #1 (Slow)

Bentonite clay has to be rehydrated prior to experimentation. 2 teaspoons of bentonite clay plus ½ cup of deionized $H_2O$ boiled at 60 degrees Celsius, then room temperature rested for four hours. Ratio: 1 Tablespoon per gallon.

Using a 3 mL graduated pipette to dilute 1 drop of rehydrated bentonite into 4.0 mL of $H_2O$.
- 100 drops (100 parts) used for experimentation. 100 drops=4.0 mL
- 3 mL capacity graduated pipette=25 drops/mL
- 25 drops/mL=0.04 mL per drop Drops of bentonite used×volume per drop=total volume of bentonite used for dilution. (1)×(0.04 mL)=0.04 mL Bentonite solute [Using the Percent Solution Equation (vol/vol %)]

$$\frac{\text{volume}}{\text{volume}}\% = \frac{\text{volume of solute}}{\text{volume of solution}} \times 100$$

$$\text{vol/vol } \% = \frac{0.04 \text{ mL bentonite}}{4.0 \text{ mL H}_2\text{O}} \times 100$$

$$\text{vol/vol } \% = 1$$

Bentonite stock solution=1% in 4.0 mL of H$_2$O for experimentation

Example 32

Bentonite Fining Agent Experimental Values—Concentration #2 (Moderate)

Bentonite clay has to be rehydrated prior to experimentation. 2 teaspoons of bentonite clay plus ½ cup of deionized H$_2$O boiled at 60 degrees Celsius, then room temperature rested for four hours. Ratio: 2 Tablespoon per gallon.

Using a 3 mL graduated pipette to dilute 2 drops of rehydrated bentonite into 4.0 mL of H$_2$O.

100 drops (100 parts) used for experimentation. 100 drops=4.0 mL 3 mL capacity graduated pipette=25 drops/mL 25 drops/mL=0.04 mL per drop Drops of bentonite used×volume per drop=total volume of bentonite used for dilution. (2)×(0.04 mL)=0.08 mL Bentonite solute [Using the Percent Solution Equation (vol/vol %)]

$$\frac{volume}{volume}\% = \frac{volume\ of\ solute}{volume\ of\ solution} \times 100$$

$$vol/vol\ \% = \frac{0.08\ mL\ bentonite}{4.0\ mL\ H_2O} \times 100$$

$$vol/vol\ \% = 2$$

Bentonite stock solution=2% in 4.0 mL of H$_2$O for experimentation

Example 33

Diatomaceous Earth Fining Agent Experimental Values—Concentration #1 (Slow)

1:100 dilution. Using a 3 mL graduated pipette to dilute 0.101 g undiluted diatomaceous earth into 12.0 mL of H$_2$O.

12.0 mL=3 times (3×) the amount of 100 drops (100 parts) used for experimentation. 100 drops=4.0 mL 3 mL capacity graduated pipette=25 drops/mL 25 drops/mL=0.04 mL per drop Per Package instructions=1 teaspoon per 1 cup of H$_2$O [Using the Percent Solution Equation (weight/vol %)]

$$\frac{weight}{volume}\% = \frac{weight\ of\ solute}{volume\ of\ solution} \times 100$$

$$w/vol\ \% = \frac{0.101\ grams\ DE}{12.0\ mL\ H_2O} \times 100$$

$$w/vol\ \% = .8$$

Sodium Alginate stock solution=0.8% in 12.0 mL of H$_2$O for experimentation

Example 34

Exemplary Solutions from Theoretical Values

Stock solutions of the compositions are made by combining the components described in the table below:

| Component | Concentration | Volume |
| --- | --- | --- |
| Pineapple (Example 1) | 0.0001% | 4.0 mL H$_2$O |
| Ginger (Example 3) | 0.0001% | 4.0 mL H$_2$O |
| Egg White (Example 5) | 0.000067% | 4.0 mL H$_2$O |
| Total | 0.000267% | 12.0 mL H$_2$O |

The stock solutions described in the table are diluted according to the following formula: Concentration×(final volume/stock volume)=volume needed from stock.

250 mL IV Bag:

0.000267%×(250 mL/12.0 mL)=0.0267×(250 mL/12.0 mL)=0.5563 mL stock solution. Accordingly, a 250 mL IV bag has 0.56 mL of the stock solution and 249.44 mL of IV specific injection water.

500 mL IV Bag:

0.000267%×(500 mL/12.0 mL)=0.0267×(500 mL/12.0 mL)=1.113 mL stock solution. Accordingly, a 500 mL IV bag has 1.113 mL of the stock solution and 498.9 mL of IV specific injection water.

Example 35

Exemplary 13.2 mL H$_2$O Stock Solution from Experimental Values

Stock solutions of the compositions are made by combining the components described in the table below:

| Component | Concentration | Volume |
| --- | --- | --- |
| Pineapple (Example 2) | 0.0001% | 4.4 mL H$_2$O |
| Ginger (Example 4) | 0.0001% | 4.4 mL H$_2$O |
| Egg White (Example 6) | 0.000067% | 4.4 mL H$_2$O |
| Total | 0.000267% | 13.2 mL H$_2$O |

The stock solutions described in the table are diluted according to the following formula: Concentration×(final volume/stock volume)=volume needed from stock.

250 mL IV Bag:

0.000267%×(250 mL/13.2 mL)=0.0267×(250 mL/13.2 mL)=0.5056 mL stock solution. Accordingly, a 250 mL IV bag has 0.51 mL of the stock solution and 249.49 mL of IV specific injection water.

500 mL IV Bag:

0.000267%×(500 mL/13.2 mL)=0.0267×(500 mL/13.2 mL)=1.011 mL stock solution. Accordingly, a 500 mL IV bag has 1.0 mL of the stock solution and 499.00 mL of IV specific injection water.

Example 36

Exemplary Solution for 250 mL IV Bag from Experimental Values

A 250 mL IV Bag is prepared from the stock solution according to the following formula: 0.000267%×(250 mL/13.2 mL)=0.0267×(250 mL/13.2 mL)=0.5056 mL Stock Solution.

Example 37

Exemplary Solution for 500 mL IV Bag from Experimental Values

A 500 mL IV Bag is prepared from the stock solution according to the following formula: 000267%×(500 mL/13.2 mL)=0.0267×(500 mL/13.2 mL)=1.011 mL Stock Solution.

500 mL IV bag=1.0 mL stock+499.00 mL IV specific injection water.

Example 38

Exemplary 250 mL IV Bag Dosages from Experimental Values

Lower Dose:
A 250 mL Lower Dose IV Bag is prepared from the stock solution according to the following formula: 0.25 mL stock solution+249.75 mL IV specific injection water (at 0.000134% concentration, ½ of medium dosage).

Medium Dose:
A 250 mL Medium Dose IV Bag is prepared from the stock solution according to the following formula: 0.51 mL stock solution+249.49 mL IV specific injection water (at 0.000267% concentration).

Higher Dose:
A 250 mL Higher Dose IV Bag is prepared from the stock solution according to the following formula: 0.76 mL stock solution+249.24 mL IV specific injection water (at 0.0004005% concentration, 1.5× times medium dosage).

Example 39

Exemplary 500 mL IV Bag Dosages from Experimental Values

Lower Dose:
A 500 mL Lower Dose IV Bag is prepared from the stock solution according to the following formula: 0.51 mL stock solution+499.49 mL IV specific injection water (at 0.000134% concentration, ½ of medium dosage).

Medium Dose:
A 500 mL Medium Dose IV Bag is prepared from the stock solution according to the following formula: 1.0 mL stock solution+499.00 mL IV specific injection water (at 0.000267% concentration).

Higher Dose:
A 500 mL Higher Dose IV Bag is prepared from the stock solution according to the following formula: 1.5 mL stock solution+498.5 mL IV specific injection water (at 0.0004005% concentration, 1.5× times medium dosage).

Example 40

Exemplary Veterinary Intramuscular 5 mL Injections

Veterinary injections are prepared using the stock solution described in Example 8 according to the following formula: 0.000267%×(5 mL/13.2 mL)=0.0267×(5 mL/13.2 mL)=0.01 mL stock solution.

A 5 mL regular dosage shot is prepared with 0.1 mL stock+4.99 mL IM specific injection water (at 0.000267% concentration).

Example 41

Exemplary Veterinary Intramuscular 10 mL Injections

Veterinary injections are prepared using the stock solution described in Example 8 according to the following formula: 0.000267%×(10 mL/13.2 mL)=0.0267×(10 mL/13.2 mL)=0.02 mL stock solution.

A 10 mL regular dosage shot is prepared with 0.2 mL stock solution+9.8 mL IM specific injection water. A 10 mL higher dosage shot is prepared with 0.3 mL stock solution+9.7 mL IM specific injection water (at 0.0004005% concentration, 1.5× times regular dose).

Example 42

Treatment of Stage III Colon Cancer

A 65 year old female patient of Vietnamese-American nationality presented with Stage II-III colon cancer. In September, 2012 the patient was diagnosed with Stage II cancer and operations were performed to remove a malignant section of her colon. Post op evaluations confirmed transition to Stage III Cancer.

Alternative treatment started January 2013. This treatment consisted of: ½ of a fresh pineapple+2 cm piece of fresh ginger root juiced to make approximately a 12 ounce cup and one over easy egg daily. The juice and egg were consumed on a daily basis for three months straight; two months prior to radiation and chemotherapy, and one month during radiation and chemotherapy.

From March 2013 to April 2013, the patient received Radiation+Chemotherapy. Radiation was received a total of 20 times and Chemotherapy was received a total of four times. In April 2013 the patient was discharged on a clean bill of health. During the Radiation+Chemotherapy treatment there were no signs of side effects.

A clean bill of health issued by specialist doctor on April 2013 and the alternative treatment was modified to twice a week only for preventive measures.

Example 43

Treatment of Stage III Uterine Cancer

A 47 year old female patient of Vietnamese nationality presented with Stage III uterine cancer. In 2013 a first surgery was performed to remove a tumor that weighed 1.6 kg and a second surgery was performed in February 2014 to remove another recurring tumor that grew in the same area.

Alternative treatment comprising ⅓ of a fresh pineapple+3-4 cm piece of fresh ginger juiced+1 raw egg white to make approximately a 12 ounce cup was administered once daily from March 2014 to April 2014. After first day of alternative treatment consumption, extreme rectal bleeding was noticed for the first day only. This treatment was consumed for one month. An April 2014 visit showed a clean bill of health with no remaining cancer cells being identified.

Example 44

Treatment of Stage 0 Breast Cancer

A 60 year old female patient of Vietnamese-American nationality presented with Stage II-III colon cancer. In September, 2012 the patient was diagnosed with Breast cancer. Surgeries were preformed to remove non-benign tumors or dense breast tissue spots. In November 2013, breast mammogram showed evidence of a few dense breast tissue spots and hyperplasia cell accumulations. Biopsy was suggested for the hyperplasia cell accumulations for malignancies.

Alternative treatment comprising ¼ of fresh pineapple+2-3 cm of fresh ginger juiced+1 raw egg to make approximately a 16 ounce cup was administered once a day, daily for only two months straight.

Prior to alternative treatment, patient had a daily fevers for 10-12+ years. No symptoms of the common cold or flu, but present fever daily and the only way to control it was to take Tylenol or Ibuprofen daily. Also during that time patient had a constant daily high blood pressure of at least 170-180 (systolic)/95-100 (diastolic). Three different blood pressure medications were taken to control the blood pressure to a normal range. One week after the alternative treatment was commenced, the patient's fever was gone and blood pressure returned to normal.

A biopsy was performed after the patient's symptoms subsided and no malignancies were tested in the dense breast tissue spots. Patient has remained cancer and symptom free since June 2014.

Example 45

Treatment of Stage IV Lung Cancer

A 73 year old male patient of Vietnamese-American nationality presented with Stage IV Lung cancer. In December 2012, the prognosis was an estimated 4 months left to live.

Beginning February 2013, 2-3 cups of an alternative treatment, each 12 ounce cup comprising ¼ of a fresh pineapple+2-4 cm piece of fresh ginger+1 raw egg white, was consumed daily for three months. The starting tumor size in the lung had a radius of 2.5 cm wide. After three months of this treatment, the tumor restaging test results showed that the tumor decreased in radius width down to 1.8 cm.

Patient went from Stage IV with chemotherapy infusions down to Stage III. At this point in the treatment, only chemotherapy pills were taken, there were no more infusions. Patient was able to function independently more, with little to no side effects anymore from the chemotherapy infusions.

Eventually, patient gave up the treatment and passed away (returned back to Stage IV, back on chemotherapy, back on side effect medications), but patient did extend life span up to 14 months more from the original prognosis of 4 months, totaling 18 months.

Example 46

Treatment of Stage III-IV Lung Cancer

A 63 year old female patient of Vietnamese-American nationality presented with Stage III-IV Lung Cancer. In 2013 the patient received the chemotherapy pill and cancer progressed from Stage I to Stage III. Patient is currently on Chemotherapy and in Stage IV.

From July 2013 to October 2013 the patient received the alternative treatment of ¼ of a fresh pineapple+3-4 cm piece of fresh ginger root juiced+1 raw egg white per 12 ounce cup, 3 times a day. Prior to alternative treatment, patient was bedridden, skin was ashy with itchy bumps, lemon sized hole in neck, severely underweight and bony. Three months of consumption resulted in a "normal" physique again; gained weight, pink fleshed skin with no itchy bumps and lesions, able to move independently with normal energy levels again.

Patient gave up the alternative treatment after October 2013 due to monotony of treatment. Cancer restaging showed that quitting led cancer to progression from III to Stage IV.

Example 47

Treatment of Stage III-IV Colon Cancer

A 68 year old female patient of Vietnamese-American nationality presented with Stage III-IV Colon Cancer. In May 2014 surgery was conducted to remove a malignant section of colon while in Stage III cancer. Post op resulted in transition to Stage IV cancer progression.

From April 2014 to the present, patient began alternative treatment of ¼ of a fresh pineapple+2-3 cm piece of fresh ginger juiced+1 raw egg white to make a 12 ounce cup, twice a day. Treatment is still ongoing.

Example 48

Treatment of Stage IV Breast+Lymph+Bone Cancer

A 64 year old female patient of Russian-American nationality presented with Stage IV Breast+Lymph+Bone Cancer. Radiation and chemotherapy were done simultaneously from April 2013 when diagnosed with stage IV breast cancer that was spreading to the lymph nodes and bone tissue.

Alternative treatment procedure is ongoing and was started May 2013. The alternate procedure included juices from 1 whole pineapple+6-7 cm piece of ginger every 2 days and 1 fresh egg white to each cup before consuming. The 12 ounces of the composition is consumed twice a day.

Example 49

Treatment of Stage IV Prostate+Lymph Cancer

A 71 year old male patient of American nationality presented with Stage IV Prostate+Lymph Cancer. Previously a surgery was performed on bladder to remove the cancerous portion but cancer is now recurring a second time.

Alternative treatment comprising 4-5 cm piece of fresh ginger juiced first, then ½ of a pineapple to make two 12-ounce cups is being used now. One cup is consumed for breakfast, the other one refrigerated for in the evening. For each cup, a single raw egg white is added and shaken up into the drink. The patient has been consuming the alternative treatment daily for more than two weeks.

Prior to alternative treatment Stage IV cancer was diagnosed with exams showing that cancer is spreading to parts of bladder, colon, lymph nodes. After two weeks of alternative treatment, PET scans show that the cancer is now localized to only the pelvic region. Patient is able to move around independently each day and appetite is normal. Treatment is still ongoing.

Example 50

Exemplary Reagents/Enzymes Tested and Results

Saltwater: Looking at ion effects, successful, works to deteriorate the extracellular matrix in patches like a fining agent.

White vinegar (acetic acid): Chosen for function as a disinfectant with low toxicity. Successful in experiment to remove extracellular matrix, however, requires a more complex dilution than proteolytic enzymes for effectiveness without rupturing the cell.

10% Liquid bleach (sodium hypochlorite): Chosen for properties of disinfectant/bleaching agent strong enough to remove blood, successful, but toxic and very slow rate to remove extracellular matrix.

Calcium hypochlorite: Chosen for properties to disinfect water and acts like a bleaching agent, safe for drinking water unlike sodium hypochlorite. Successful in experiment, removes extracellular matrix, however, at a much slower rate than proteolytic enzymes.

Pineapple (Bromelain+Actinidain): Successful, but requires a dilution for safe effectiveness to not destroy entire cell. Once optimal concentration is reached, slowly shows observable differences to extracellular matrix over time.

Powdered Bromelain (meat tenderizer): Alternative to using fresh pineapple, not successful as it did not achieve the desired effect of removing the extracellular matrix, but rather only damaged cells.

Ginger root (GP/Zingipain): Alternative to using fresh pineapple, chosen for proteolytic enzyme properties. Successful in removing extracellular matrix and performs at about a similar rate as the fresh pineapple does, but requires dilution.

Turmeric: Chosen for its properties to heal wounds and lighten scars.

3% $H_2O_2$ (hydrogen peroxide): Chosen for disinfecting and bleaching properties to surfaces and wounds. Not successful for removing extracellular matrix, as it showed no effect on it.

UV: Chosen as a demonstration to what UV (and the idea of a treatment) can do to the cell—obliterates shell and embryo before hatching.

Egg white (albumen): Although a protein itself, chosen for its known properties of a winemaking fining agent to remove impurities while being nontoxic to the wine. Successful in experiment, requires dilution and a very small ratio used to not overpower its usage.

70% ethanol: Chosen for disinfectant properties, not successful, damaged cell completely.

Decolorizer: Chosen for dye removal properties in microbiology staining tests, while keeping the cell studied intact. Successful in removing extracellular matrix, however, requires dilution, slow rate of extracellular matrix deterioration.

Acid Alcohol (acetone): Chosen for cleaning and peeling properties, proved to be unsuccessful as cell was severely damaged.

Powdered Urea: Chosen for its functions in kidneys to remove nitrogenous wastes. Successful in removing the extracellular matrix, but requires a tough dilution for effectiveness.

Ammonia: Chosen for cleaning properties and similar to that of urea, but more motile than urea is. Successful, but tough dilution.

Sodium bicarbonate (baking soda): Chosen for cleaning and leavening properties with low toxicity as it can be consumed. Effective in removing extracellular matrix, however, at a very slow rate.

Purigen: Used because of its properties to remove impurities in water as well as removing nitrogenous organic waste in fish tanks. Since it is safe to use in the presence of fish, it would have similar effectiveness as the proteolytic enzymes in the presence of brine shrimp.

What is claimed is:

1. A method for treating cancer comprising administering to a human cancer patient an effective amount of an intravenous composition comprising two or more proteolytic enzymes selected from the group consisting of bromelain, Ginger Protease (GP), zingipain, papain, chymopaypain, and ficain and one fining agent selected from the group consisting of isinglass (ichtoyocolle), kieselsol, albumen, chitosan, sodium alginate, bentonite, or diatomaceous earth for treating cancer.

2. The method of claim 1, wherein the cancer is selected from the group consisting of colon cancer, uterine cancer, breast cancer, lung cancer, bone cancer, and prostate cancer.

3. The method of claim 1, wherein the composition is administered twice a day.

4. The method of claim 1, wherein the composition is administered at least once a day.

* * * * *